(12) United States Patent
Forrester et al.

(10) Patent No.: US 11,179,413 B2
(45) Date of Patent: Nov. 23, 2021

(54) METHODS OF TREATMENT OF CANCER WITH REDUCED UBB EXPRESSION

(71) Applicant: Novartis AG, Basel (CH)

(72) Inventors: William C. Forrester, Cambridge, MA (US); Alexia T. Kedves-Volpe, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/491,660

(22) PCT Filed: Mar. 5, 2018

(86) PCT No.: PCT/IB2018/051408
§ 371 (c)(1),
(2) Date: Sep. 6, 2019

(87) PCT Pub. No.: WO2018/163051
PCT Pub. Date: Sep. 13, 2018

(65) Prior Publication Data
US 2020/0206256 A1 Jul. 2, 2020

Related U.S. Application Data

(60) Provisional application No. 62/467,480, filed on Mar. 6, 2017.

(51) Int. Cl.
| | | |
|---|---|---|
| *C07H 21/04* | (2006.01) | |
| *A61K 31/7105* | (2006.01) | |
| *A61P 35/00* | (2006.01) | |
| *A61K 33/243* | (2019.01) | |
| *C12N 15/113* | (2010.01) | |
| *C12Q 1/6886* | (2018.01) | |

(52) U.S. Cl.
CPC ........ *A61K 31/7105* (2013.01); *A61K 33/243* (2019.01); *A61P 35/00* (2018.01); *C12N 15/113* (2013.01); *C12Q 1/6886* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

FOREIGN PATENT DOCUMENTS

| KR | 20150016816 A | 2/2015 |
|---|---|---|
| WO | WO2011080314 A2 | 7/2011 |

OTHER PUBLICATIONS

Yin, Fuqiang, et al. ("Tumor suppressor genes associated with drug resistance in ovarian cancer." Oncology reports 30.1 (2013): 3-10).*
UBC Genbank Sequence (PubMed accessed Feb. 23, 2021).*
International Search Report dated May 2, 2018.
Yiting Tang, et al., "Downregulation of ubiquitin inhibits the proliferation and radioresistance of non-small cell lung cancer cells in vitro and in vivo," Scientific Reprots, vol. 5, No. 1, Mar. 30, 2015.
Choongseob Oh, et al., "Downregulation of ubiquitin level via knockdown of polyubiquitin gene Ubb as potential cancer therapeutic intervention," Scientific Reports, vol. 3, No. 1, Sep. 11, 2013.
Alexia T. Kedves, et al., "Recurrent ubiquitin B silencing in gynecological cancers establishes dependence on ubiquitin C," Journal of Clinical Investigation, vol. 127, No. 12, Dec. 1, 2017, pp. 4554-4568.
Pagliarini, Raymond et al., "Oncogene addiction: pathways of therapeutic response, resistance, and road maps towards a cure", EMBO reports, vol. 16, No. 3, 2015, 17 pages.
McLornan, Donal P. et al., "Applying Synthetic Lethality for the Selective Targeting of Cancer", The New England Journal of Medicine 371:18, Oct. 30, 2014, 11 pages.
Bitler, Benjamin G. et al., "Synthetic lethality by targeting EZH2 methyltransferase activity in ARID1A-mutated cancers", Nature Medicine, vol. 21, No. 3, Mar. 2015, 10 pages.
Van den Bent, Martin J., "Interobserver variation of the histopatholigical diagnosis in clinical trials on glioma: a clinician's perspective", Acta Neuropathol (2010) 120: 297-304, 8 pages.
Verhaak, Roel G.W. et al., "Integrated Genomic Analysis Identifies Clinically Relevant Subtypes of Glioblastoma Characterized by Abnormalities in PDGFRA, IDH1, EGFR, and NF1", Cancer Cell 17, 98-110, Jan. 19, 2010, 13 pages.
Parsons, D Williams et al., "An Integrated Genomic Analysis of Human Glioblastoma Multiforme", Science vol. 321, Sep. 26, 2008, 7 pages.
Dang, L. et al., "IDH mutations in cancer and progress toward development of targeted therapeutics", Annals of Oncology 27: 599-608, 2016, 10 pages.
Loehrer, Patrick J. et al., "Cisplatin", Diagnosis and Treatment Drugs Five Years Later, Annals of Internal Medicine. 1984; 100: 704-713, 10 pages.
Verhaak, Roel G.W. et al., "Prognostically relevant gene signatures of high-grade serous ovarian carcinoma", The Journal of Clinical Investigation, 2013; 123(1): 517-525, 10 pages.
Zhang, Hui et al., "Integrated Proteogenomic Characterization of Human High-Grade Serous Ovarian Cancer", Cell 166, Jul. 28, 2016, 755-765, 12 pages.
Winterhoff, Boris et al., "Molecular classification of high grade endometrioid and clear cell ovarian cancer using TCGA gene expression signatures", Gynecologic Oncology 141 (2016) 95-100, 6 pages.
Kim, Geoffrey et al., "FDA Approval Summary: Olaparib Monotherapy in Patients with Deleterious Germline BRCA-Mutated Advanced Ovarian Cancer Treated with Three or More Lines of Chemotherapy", Published OnlineFirst, Jul. 17, 2015, 6 pages.
Lord, Christopher J. et al., "Synthetic Lethality and Cancer Therapy: Lessons Learned from the Development of PARP Inhibitors", Annual Review of. Medicine 2015, 66:455-70, 19 pages.

(Continued)

*Primary Examiner* — Kimberly Chong
(74) *Attorney, Agent, or Firm* — Crowell & Moring LLP; Yuezhong Feng

(57) ABSTRACT

The present invention provides compositions comprising a UBC antagonist and methods of use thereof for treating cancer in a patient. In some embodiments, the cancer patient may have a reduced expression level of a UBB gene product. Further provided are reagents and methods for detection of a UBB and/or UBC gene product.

12 Claims, 13 Drawing Sheets

Specification includes a Sequence Listing.

(56) References Cited

OTHER PUBLICATIONS

Wilborg, Ove et al., "The human ubiquitin multigene family: some genes contain multiple directly repeated ubiquitin coding sequences", The EMBO Journal vol. 4 No. 3 pp. 755-759, 1985, 5 pages.
Barretina, Jordi et al., "The Cancer Cell Line Encyclopedia enables predictive modelling of anticancer drug sensitivity", Nature, vol. 483, Mar. 29, 2012, 8 pages.
Ryu, Kwon-Yul et al., "The mouse polyubiquitin gene UbC is essential for fetal liver development, cell-cycle progression and stress tolerance", The EMBO Journal (2007) 26, 2693-2706, 14 pages.
Liu, Xiaoqi et al., "Activation of Cdc2/cyclin B and inhibition of centrosome amplification in cells depleted of Plk1 by siRNA", PNAS Jun. 25, 2002, vol. 99 No. 13, 8672-8676, 5 pages.
Nijhawan, Deepak et al., "Cancer Vulnerabilities Unveiled by Genomic Loss", Cell 150, 842-854, Aug. 17, 2012, 13 pages.
Solimini, Nicole L et al., "Recurrent Hemizygous Deletions in Cancers May Optimize Proliferative Potential", NIH Public Access, Author Manuscript, Science, May 20, 2014, 12 pages.
Claessen, Jasper H.L. et al., "Protein quality control in the ER: balancing the ubiquitin checkbook", Trends in Cell Biology, Jan. 2012, vol. 22, No. 1, 11 pages.
Al-Hakim, Abdallah et al., "The ubiquitous role of ubiquitin in the DNA damage Yesponse", DNA Repair 9 (2010) 1229-1240, 12 pages.
Moldovan, George-Lucian et al., "How the Fanconi Anemia Pathway Guards the Genome", Annual Review Genetics, 2009, 43:223-49, 29 pages.
Paulsen, Renee D. et al., "A Genome-wide siRNA Screen Reveals Diverse Cellular Processes and Pathways that Mediate Genome Stability", Molecular Cell 35, 228-239, Jul. 31, 2009, 12 pages.
Stewart, Grant S., "Solving the RIDDLE of 53BP1 recruitment to sites of damage", Cell Cycle 8:10, 1532-1538, May 15, 2009, 7 pages.
Stewart, Grant S. et al., "The RIDDLE Syndrome Protein Mediates a Ubiquitin-Dependent Signaling Cascade at Sites of DNA Damage", Cell 136, 420-434, Feb. 6, 2009, 15 pages.
Park, Hyejin et al., "Disruption of polyubiquitin gene Ubc leads to defective proliferation of hepatocytes and bipotent fetal liver epithelial progenitor cells", Biochemical and Biophysical Research Communications 435 (2013) 434-440, 7 pages.
Ryu, Kwon-Yul et al., "Perturbation of the Hematopoietic System during Embryonic Liver Development Due to Disruption of Polyubiquitin Gene Ubc in Mice", PLoS ONE, Feb. 2012, vol. 7, Issue 2, 9 pages.
Sinnar, Shamim A. et al., "Altered Testicular Gene Expression Patterns in Mice Lacking the Polyubiquitin Gene Ubb", Molecular Reproduction & Development 78:415-425 (2011), 11 pages.
Goldberg, Michael S. et al., "Nanoparticle-mediated delivery of siRNA targeting Parp1 extends survival of mice bearing tumors derived from Brca1-deficient ovarian cancer cells", PNAS, Jan. 11, 2011, vol. 108, No. 2, 745-750, 6 pages.
Zuckerman, Jonathan E. et al., "Clinical experiences with systemically administered siRNA-based therapeutics in cancer", Nature Review Drug Discovery, vol. 14, Dec. 2015, 14 pages.
Bennett, C. Frank et al., "Pharmacology of Antisense Drugs", Annu. Rev. Pharmacol, Toxicol. 2017, 57:81-105, 28 pages.
McClorey, Graham et al., "An overview of the clinical application of antisense oligonucleotides for RNA-targeting therapies", Current Opinion in Pharmacology 2015, 24:52-58, 7 pages.
Helming, Katherine C et al., "ARID1B is a specific vulnerability in ARID1A-mutant cancers", Nature Medicine, vol. 20, No. 3, Mar. 2014, 5 pages.
Hoffman, Gregory R., et al., "Functional epigenetics approach identifies BRM/SMARCA2 as a critical synthetic lethal target in BRG1-deficient cancers", PNAS, Feb. 25, 2014, vol. 111, No. 8, 6 pages.
Oike, Takahiro et al., "A Synthetic Lethality-Based Strategy to Treat Cancers Harboring a Genetic Deficiency in the Chromatin Remodeling Factor BRG1", Cancer Res; 73(17) Sep. 1, 2013, 12 pages.
Kadoch, Cigall, "Lifting Up the HAT: Synthetic Lethal Screening Reveals a Novel Vulnerability at the CBP-p300 Axis", Cancer Discovery, Apr. 2016, 4 pages.
Ogiwara, Hideaki et al., "Targeting p300 Addiction in CBP-Deficient Cancers Causes Synthetic Lethality by Apoptotic Cell Death due to Abrogation of MYC Expression", OnlineFirst Nov. 24, 2015, 17 pages.
Schmittgen, Thomas D. et al., "Analyzing real-time PCR data by the comparative $C_T$ method", Nature Protocols vol. 3 No. 6, 2008, 8 pages.
Weinstein, John N. et al., "The Cancer Genome Atlas Pan-Cancer analysis project", Nature Genetics vol. 45, No. 10, Oct. 2013, 8 pages.
Li, Bo et al., "RSEM: accurate transcript quantification from RNA-Seq data with or without a reference genome", BMC Bioinformatics 2011 12:323, 16 pages.
Ardlie, Kristin G. et al., GTEx Consortium, "The Genotype-Tissue Expression (GTEx) pilot analysis: Multitissue gene regulation in humans", HHS Public Access Author manuscript Science. Available in PMC Aug. 24, 2015, 33 pages.
Fraley, Chris et al., "mclust Version 4 for R: Normal Mixture Modeling for Model-Based Clustering, Classification, and Density Estimation", Technical Report No. 597, Department of Statistics, University of Washington, Seattle, WA 98195-4322 USA, Jun. 2012, 57 pages.
Therneau, Terry M., "A Package for Survival Analysis in S", Mayo Foundation, Feb. 1999, 83 pages.
Scheng, Qing et al., "An Activated ErbB3/NRG1 Autocrine Loop Supports In Vivo Proliferation in Ovarian Cancer Cells", Cancer Cell 17, 298-310, Mar. 16, 2010, 13 pages.
Chojnacki, Michal, et al., "Characterizing polyubiquitinated forms of the neurodegenerative ubiquitin mutant $UBB^{+1}$", FEBS Press Letters 590 (2016) 4573-4585, 13 pages.

* cited by examiner

FIGURE 1a,b
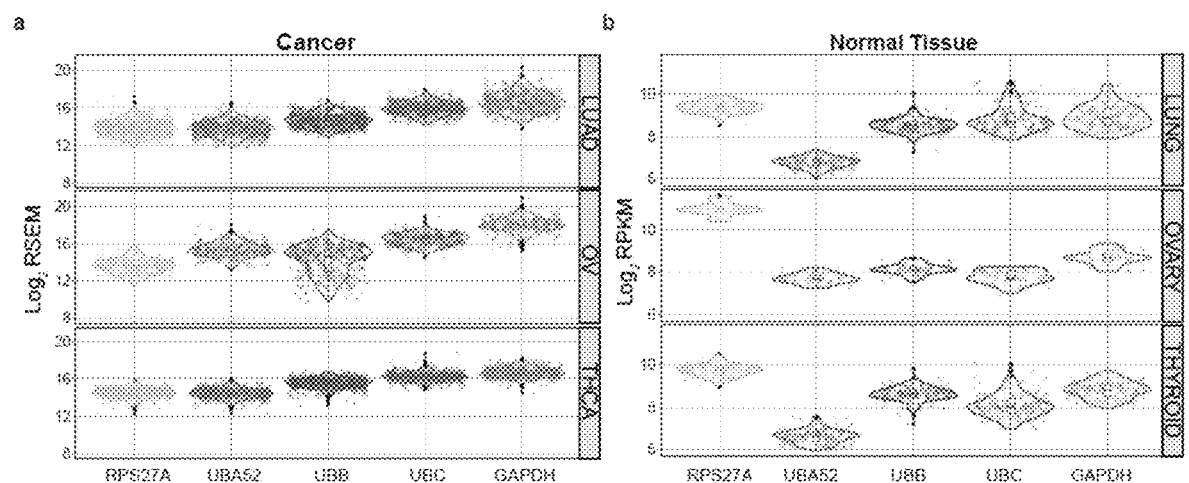

FIGURE 1c,d
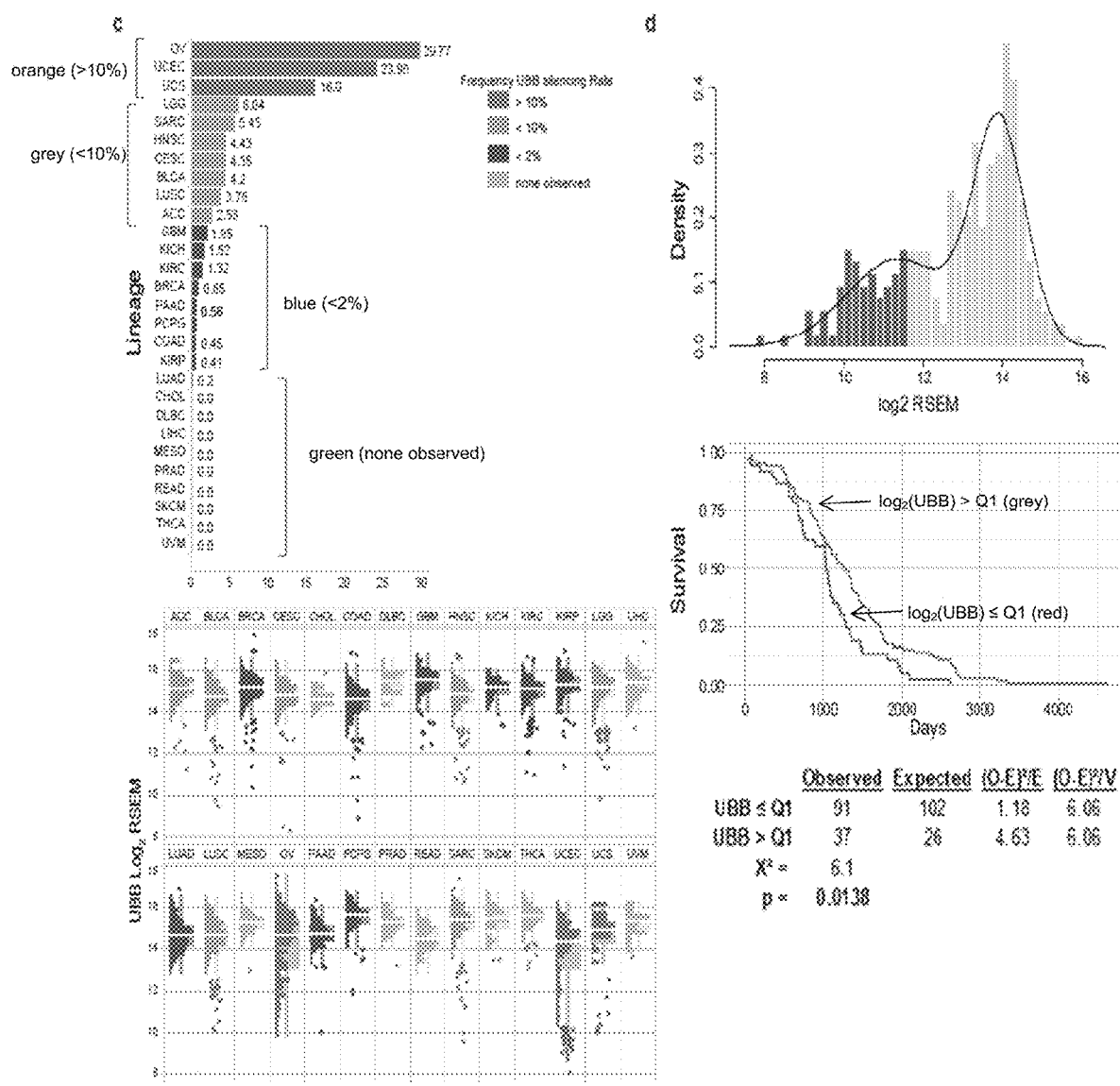

FIGURE 2a,b
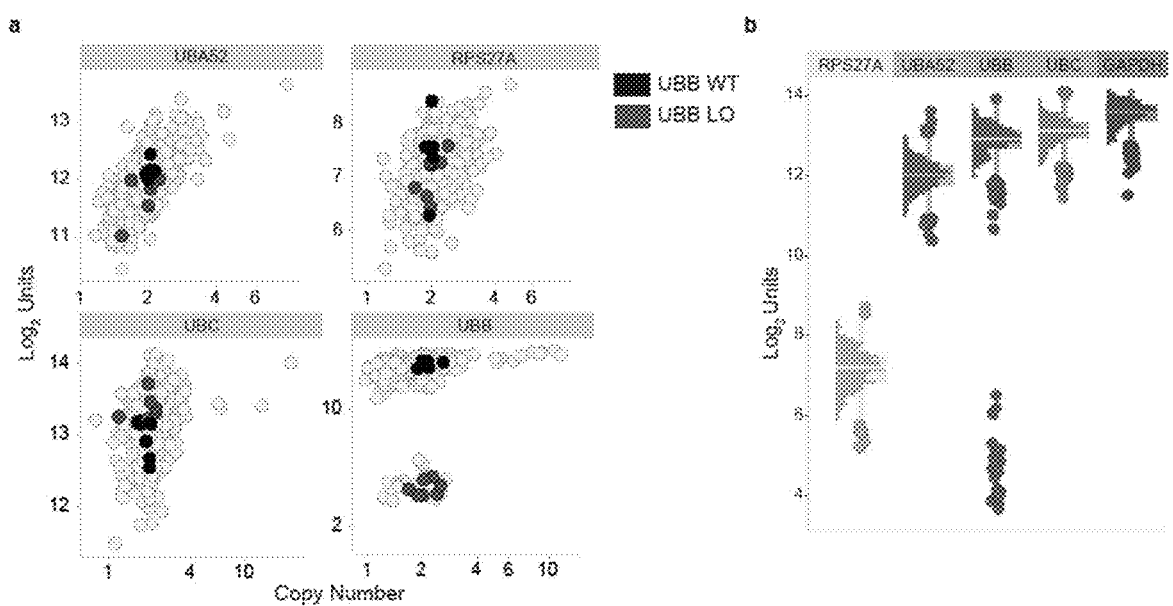

FIGURE 2c,d
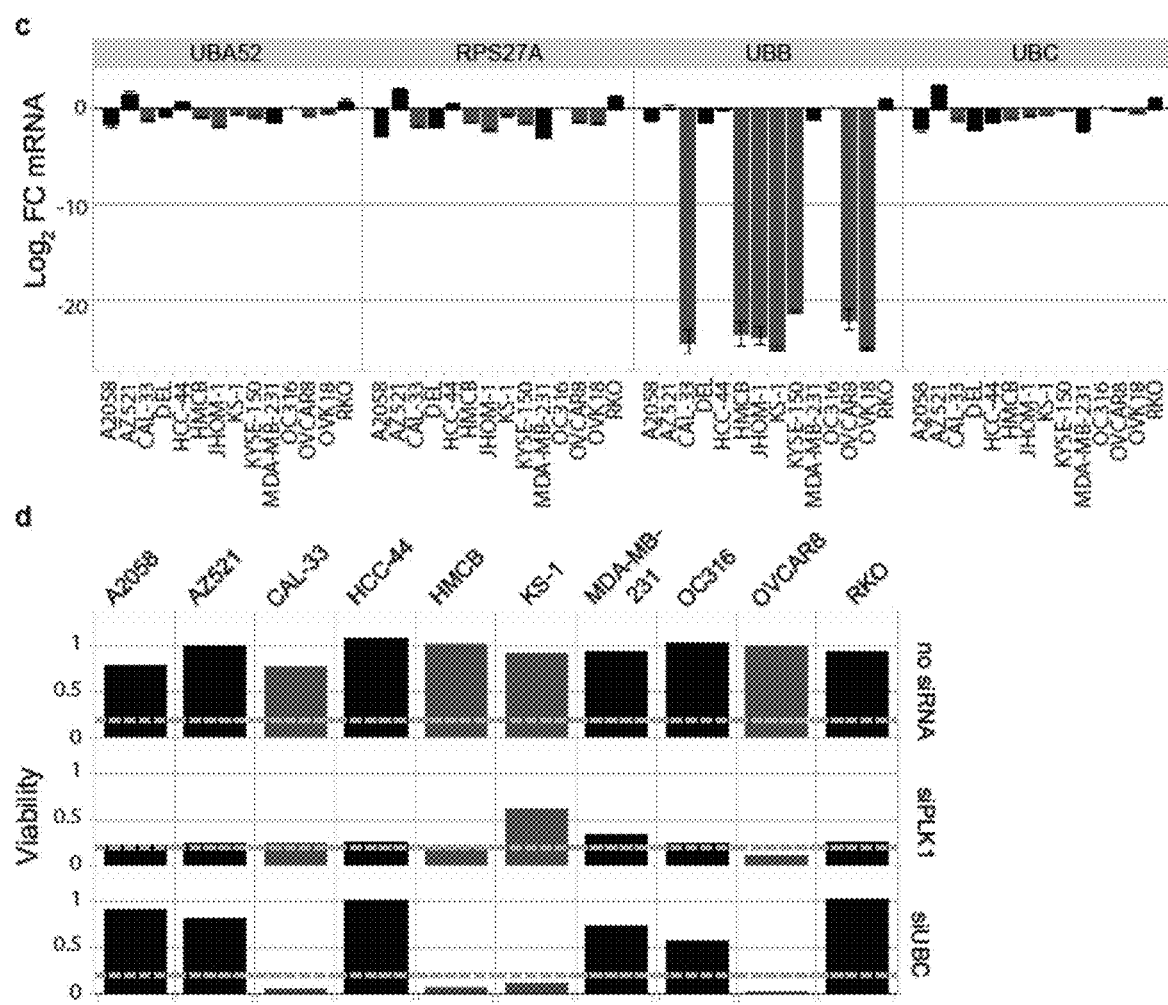

METHODS OF TREATMENT OF CANCER WITH REDUCED UBB EXPRESSION

This application claims the benefit of U.S. Provisional Application No. 62/467,480 filed on Mar. 6, 2017, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 27, 2018, is named PAT057547-WO-PCT_SL.txt and is 6,303 bytes in size.

FIELD OF THE DISCLOSURE

The present disclosure relates to compositions of a ubiquitin C (UBC) antagonist and methods of use thereof in the treatment of cancer patients having a reduced expression level of a ubiquitin B (UBB) gene product. Further disclosed are reagents for determining the expression level of the UBB/UBC gene product and methods of use thereof for predicting and prognosing responsiveness of a cancer patient to treatment with a UBC antagonist.

BACKGROUND

Target discovery in oncology has focused predominantly on two basic principles: oncogene addiction (Pagliarini, et al., 2015) and synthetic lethality (McLornan, et al., 2014). Identifying cancer-specific gain-of-function alterations in oncogenes such as ABL, BRAF, EGFR, and PI3K has fueled the development of potent and selective kinase inhibitors that antagonize the addiction of cancer cells to a defined oncogenic driver or pathway. By contrast, loss-of-function mutations, most notably in tumor suppressor genes, are not readily druggable, motivating the search for synthetic lethal targets (Bitler, et al., 2015).

These approaches are complemented by large-scale bioinformatic analysis of tumor profiling data. Coordinated, large-scale efforts to catalog several measurable features of tumor cells—including copy number alterations, mutations, expression, and epigenetic states—have enabled the classification of patients into specific disease subsets as well as the identification of new, actionable targets. Glioblastoma, once a diagnosis based on anatomy and histopathology (van den Bent, 2010) was separable into subtypes based on genetic alterations, expression signatures, and long-term survival (Verhaak, et al., 2010; Parsons, et al., 2008). This approach also found that a subset of patients with gain-of-function mutations in a gene that had not previously been linked to cancer, IDH1 (Parsons, et al., 2008), leading to the development of inhibitors that are being investigated in clinical trials (Dang, et al., 2016).

Such new approaches are imperative because there are many cancer patients for whom treatment options have not substantively changed. The mainstay treatment for women with ovarian cancer remains cisplatin, which was introduced in the late 1970's (Loehrer, et al., 1984), and survival rates have remained effectively unchanged since. While profiling in ovarian cancer has led to important insights for the molecular classification of ovarian cancer subtypes, there persists a gap at the level of finding lesions that are validated as clinically relevant targets in these patients (Verhaak, et al., 2013; Zhang, et al., 2016; Winterhoff, et al., 2016). Synthetic lethality, perhaps based on tumor suppressor loss, is thus a very attractive approach. Indeed, PARP inhibitors were recently approved for the treatment of a subset of ovarian cancer patients who harbor BRCA mutations (Kim, et al., 2015; Lord, et al., 2015).

SUMMARY

Some embodiments disclosed herein provide methods of treating cancer in a patient comprising: (a) identifying a patient having cancer with a reduced expression level of a ubiquitin B (UBB) gene product; and (b) administering to the patient a ubiquitin C (UBC) antagonist. In some embodiments, the UBC antagonist is an anti-sense nucleic acid, a short hairpin RNA (shRNA) or a short inhibitory RNA (siRNA). In some embodiments, the shRNA targets the nucleic acid sequence set forth in SEQ ID NO: 1, In some embodiments, the UBC antagonist is a compound. In some embodiments, the UBC antagonist is a small molecule compound. In some embodiments, the cancer is selected from the group consisting of uterine sarcoma, endometrial carcinoma, and ovarian adenocarcinoma. In some embodiments, the UBB gene product is an mRNA. In some embodiments, the UBB gene product is a protein. In some embodiments, the methods comprise measuring the copy number of the UBB gene in a sample of the patient. In some embodiments, the methods comprise measuring the expression level of the UBB gene product in a sample of the patient. In some embodiments, the methods comprise measuring the expression level of the UBB gene product by sequencing, RT-PCR, qPCR, Northern blotting, Western blotting, microarray hybridization, ELISA, in situ hybridization, or any combination thereof. In some embodiments, the sample is selected from the group consisting of a blood sample, a urine sample, a tissue sample, a biopsy sample, and any combination thereof.

Some embodiments disclosed herein provide methods of treating cancer in a patient comprising: (a) identifying a patient having cancer with a ratio of an expression level of a ubiquitin C (UBC) gene product to an expression level of a ubiquitin B (UBB) gene product that is greater than 1.25; and (b) administering to the patient a ubiquitin C (UBC) antagonist. In some embodiments, the ratio of the expression level of the UBC gene product to the expression level of the UBB gene product is greater than 2. In some embodiments, the UBC antagonist is an anti-sense nucleic acid, a short hairpin RNA (shRNA) or a short inhibitory RNA (siRNA). In some embodiments, the shRNA targets the nucleic acid sequence set forth in SEQ ID NO: 1, In some embodiments, the UBC antagonist is a compound. In some embodiments, the UBC antagonist is a small molecule compound. In some embodiments, the cancer is selected from the group consisting of uterine sarcoma, endometrial carcinoma, and ovarian adenocarcinoma. In some embodiments, the UBB gene product is an mRNA. In some embodiments, the UBB gene product is a protein. In some embodiments, the methods comprise measuring the copy number of the UBB gene in a sample of the patient. In some embodiments, the methods comprise measuring the expression level of the UBB gene product in a sample of the patient. In some embodiments, the methods comprise measuring the expression level of the UBB gene product by sequencing, RT-PCR, qPCR, Northern blotting, Western blotting, microarray hybridization, ELISA, in situ hybridization, or any combination thereof. In some embodiments, the sample is selected from the group consisting of a blood sample, a urine sample, a tissue sample, a biopsy sample, and any combination thereof.

Some embodiments disclosed herein provide methods of treating a patient having cancer, comprising administering to the patient a therapeutically effective amount of a ubiquitin C (UBC) antagonist. In some embodiments, the methods comprise identifying a patient having a reduced expression level of the ubiquitin B (UBB) gene product. In some embodiments, the methods comprise identifying a patient having a ratio of an expression level of a ubiquitin C (UBC) gene product to an expression level of a ubiquitin B (UBB) gene product that is greater than 1.25. In some embodiments, the cancer is selected from the group consisting of uterine sarcoma, endometrial carcinoma, and ovarian adenocarcinoma. In some embodiments, the cancer is ovarian adenocarcinoma. In some embodiments, the methods comprise measuring the copy number of the UBB gene in a sample of the patient. In some embodiments, the methods comprise measuring the expression level of the UBB gene product or the expression level of the UBC gene product in a sample of the patient. In some embodiments, the methods comprise administering to the patient a chemotherapeutic drug. In some embodiments, the chemotherapeutic drug is cisplatin. In some embodiments, the chemotherapeutic drug causes a DNA damage response (DDR) in the patient.

Some embodiments disclosed herein provide methods of sensitizing a patient having cancer for a chemotherapy treatment comprising administering to the patient a ubiquitin C (UBC) antagonist. In some embodiments, the chemotherapy treatment comprises administering cisplatin to the patient. In some embodiments, the UBC antagonist is an anti-sense nucleic acid, a short hairpin RNA (shRNA) or a short inhibitory RNA (siRNA). In some embodiments, the shRNA targets the nucleic acid sequence set forth in SEQ ID NO: 1, In some embodiments, the UBC antagonist is a compound. In some embodiments, the UBC antagonist is a small molecule compound. In some embodiments, the small molecule compound specifically binds to the UBC mRNA.

Some embodiments disclosed herein provide pharmaceutical compositions for treating cancer in a patient comprising a therapeutically effective amount of a ubiquitin C (UBC) antagonist and an excipient. In some embodiments, the UBC antagonist is an anti-sense nucleic acid, a short hairpin RNA (shRNA) or a short inhibitory RNA (siRNA). In some embodiments, the shRNA targets the nucleic acid sequence set forth in SEQ ID NO: 1, In some embodiments, the UBC antagonist is a compound. In some embodiments, the UBC antagonist is a small molecule compound. In some embodiments, the small molecule compound specifically binds to the UBC mRNA.

Some embodiments disclosed herein provide pharmaceutical compositions for use in treating cancer in a patient, characterized in that: (a) a patient is identified as having cancer with reduced expression level of a ubiquitin B (UBB) gene product or having a ratio of an expression level of a ubiquitin C (UBC) gene product to an expression level of a ubiquitin B (UBB) gene product that is greater than 1.25; and (b) a pharmaceutical composition comprising a therapeutically effective amount of a ubiquitin C (UBC) antagonist is administered to the patient.

Some embodiments disclosed herein provide methods of predicting or prognosing responsiveness to a treatment by a cancer patient, comprising: (a) contacting a sample from the cancer patient with a reagent that specifically binds to a ubiquitin B (UBB) gene or product thereof to form a binding complex; (b) measuring the amount of the binding complex; and (c) determining the responsiveness to the treatment by the cancer patient using the amount of the binding complex, wherein the treatment comprises administering a ubiquitin C (UBC) antagonist to the cancer patient. In some embodiments, the reagent comprises a nucleic acid molecule. In some embodiments, the reagent comprises an antibody. In some embodiments, the reagent comprises a label. In some embodiments, the label is a fluorescent label. In some embodiments, the methods comprise administering a therapeutically effective amount of the UBC antagonist to the cancer patient if the cancer patient is determined to be responsive to the treatment. In some embodiments, the methods comprise administering a chemotherapeutic drug to the cancer patient. In some embodiments, the chemotherapeutic drug is cisplatin. In some embodiments, the amount of the binding complex is indicative of the copy number of the UBB gene in the sample. In some embodiments, the amount of the binding complex is indicative of the expression level of a UBB gene product in the sample. In some embodiments, the methods further comprise determining the expression level of a UBC gene product in the sample and determining the responsiveness to the treatment by the cancer patient using the expression level of a UBC gene product and the expression level of a UBB gene product. In some embodiments, the methods comprise administering a therapeutically effective amount of the UBC antagonist to the cancer patient if the cancer patient is determined to have a ratio of the expression level of a UBC gene product to the expression level of a UBB gene product that is greater than 1.25.

Some embodiments disclosed herein provide uses of a reagent that specifically binds to a ubiquitin B (UBB) gene or product thereof for predicting or prognosing responsiveness to a treatment by a cancer patient, wherein the treatment comprises administering a ubiquitin C (UBC) antagonist to the cancer patient. In some embodiments, the uses comprise (a) contacting a sample from the cancer patient with a reagent that specifically binds to a ubiquitin B (UBB) gene or product thereof to form a binding complex; (b) measuring the amount of the binding complex; and (c) determining the responsiveness to the treatment by the cancer patient using the amount of the binding complex. In some embodiments, the uses comprise administering a therapeutically effective amount of the UBC antagonist to the cancer patient if the cancer patient is determined to be responsive to the treatment. In some embodiments, the uses further comprise administering a chemotherapeutic drug to the cancer patient. In some embodiments, the chemotherapeutic drug is cisplatin. In some embodiments, the amount of the binding complex is indicative of the copy number of the UBB gene in the sample. In some embodiments, the amount of the binding complex is indicative of the expression level of a UBB gene product in the sample. In some embodiments, the uses further comprise determining the expression level of a UBC gene product in the sample and determining the responsiveness to the treatment by the cancer patient using the expression level of a UBC gene product and the expression level of a UBB gene product. In some embodiments, the uses comprise administering a therapeutically effective amount of the UBC antagonist to the cancer patient if the cancer patient is determined to have a ratio of the expression level of a UBC gene product to the expression level of a UBB gene product that is greater than 1.25.

BRIEF DESCRIPTION OF THE DRAWINGS

FIG. 1. TCGA analysis identifies UBB silencing as a recurring lesion and a predictor of poor outcomes in ovarian cancer. (a) Expression of the four genes encoding ubiquitin is shown, along with GAPDH, from three representative tissue-specific tumor types, Lung (LUAD), Ovarian (OV) and Thyroid (THCA). RNAseq data is displayed as $\log_2$ (RSEM) values in violin plots encompassing box plots and kernel density estimate plots. UBB expression (red) shows a broad distribution range exclusively in ovarian cancer patient samples. (b) Expression of same genes in corresponding normal tissue. (c) Top. The percentage of samples with a UBC:UBB ratio greater than 1.25 (the upper inner fence, a standard statistical measure of outlier status, defined as Q3+1.5*IQ indicates that the majority of UBB silencing is found among tumors localized to the female reproductive system, with moderate to rare UBB reductions in other tumor types. Bottom. UBB expression in TCGA-study tissues highlights the distribution of UBB outliers in solid tumors (orange=high silencing rate>10%, grey=moderate<10%, blue=rare<2%, green=none observed). (d) Top. Kernel density estimates of $\log_2$(UBB) expression levels in TCGA ovarian tumors illustrate the bimodal distribution of expression. Bottom. A Kaplan-Meier plot of ovarian cancer patient survival stratified by the first quartile of UBB expression (red=$\log_2$(UBB)<Q1, grey=$\log_2$(UBB)>Q1) demonstrates significantly poorer outcomes in patients with UBB-silenced tumors.

FIG. 2. Ubiquitin expression and synthetic lethality. (a) Copy number vs Expression plots for each of the genes encoding ubiquitin across all 1,053 cell lines from the CCLE. Note that the range of Y-axis values in $\log_2$(RSEM) is set based on the expression range specific for each gene. The cell lines highlighted were selected for additional analysis to validate levels of ubiquitin expression. Lines selected for subsequent analysis included those predicted to express UBB at low (red) or high (black) levels. (b) Box plots of data from (a) show expression as a unimodal distribution for all ubiquitin genes except for UBB, which exhibits a substantial outlier population. GAPDH is included as a control. (c) Analysis of RNA levels for each of the ubiquitin-encoding genes by qPCR. Cell lines were cultured, and RNA was analyzed by RT-qPCR using primers specific for each of the four human ubiquitin-encoding genes. Results of technical quadruplicates confirm the CCLE profiling data. (d) Transfections performed with siRNAs for PLK1 and UBC are shown. Top row ("no siRNA") reflects a mock transfection lacking only siRNA. All data is normalized to NT siRNA control (not included), and viability was measured after 72 hours using Cell Titer Glo.

DEFINITIONS

Figure 3:
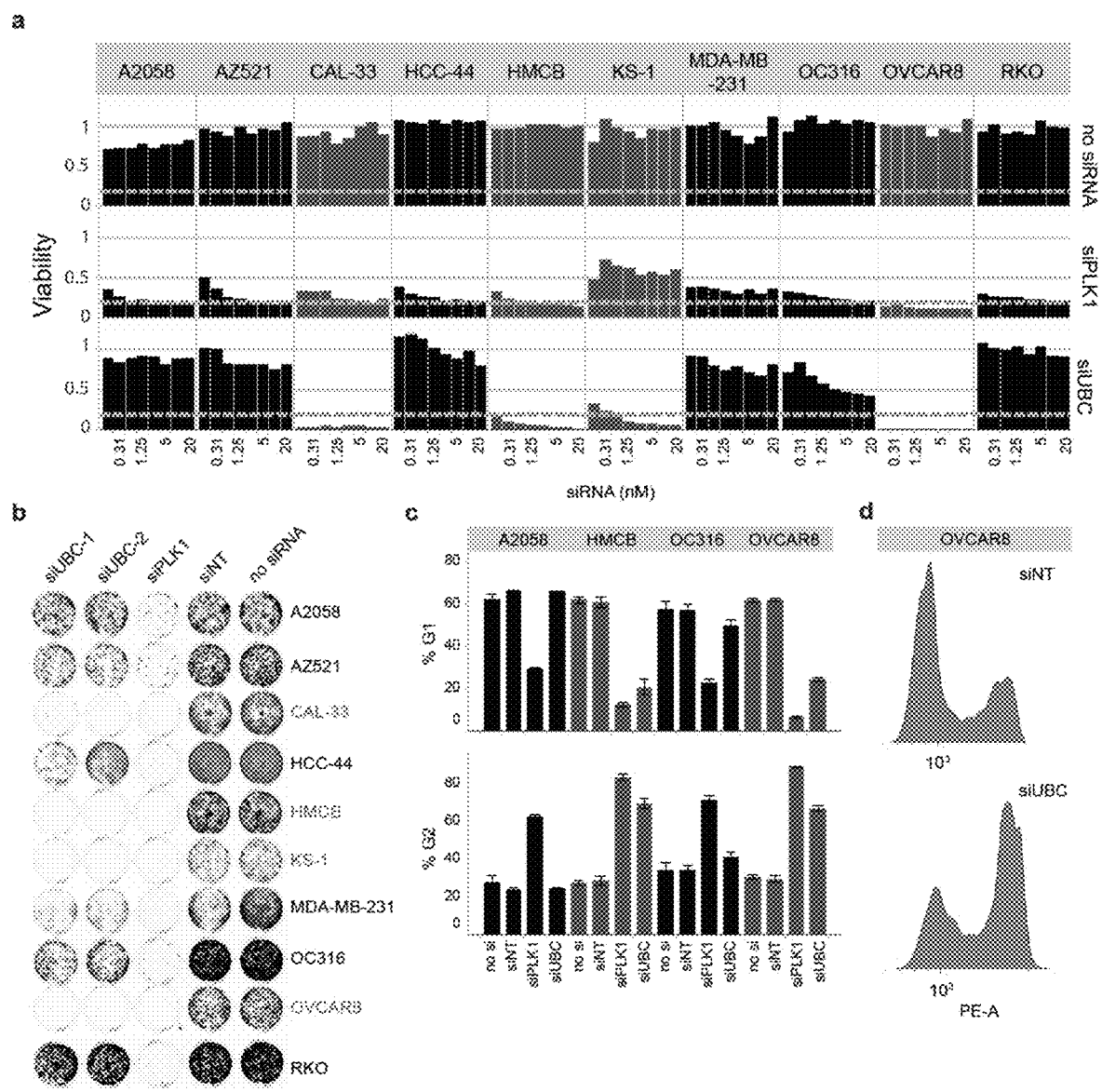
FIG. 3. Long-term viability and cell cycle effects of UBC knockdown. (a) PLK1 and UBC siRNAs were titrated and transfected into UBB$^{WT}$ (black) and UBB$^{LO}$ (red) cells. Final concentrations of target siRNA ranged from 0.16-20 nM and included a complementary amount of control NT siRNA needed for a total final concentration of 20 nM. (b) Colony formation assays following transfection with siRNAs for UBC, PLK1, NT, and no siRNA are shown. After 14 days, cells were fixed and stained with crystal violet. (c) Cell cycle analysis 30 hours after transfection of UBB$^{WT}$ and UBB$^{LO}$ cells with siRNAs against PLK1, UBC, NT, or no siRNA controls. Distribution across the cell cycle is shown as percent G1 (top) and G2 (bottom) with standard deviation. (d) A histogram of DNA content per cell is shown for OVCAR8 transfected with NT siRNA control (top) and UBC siRNA (bottom).

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

A "probe" when used in the context of polynucleotide manipulation refers to an oligonucleotide that is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to, radioisotopes, fluorochromes, chemiluminescent compounds, dyes, and proteins, including enzymes.

A "primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in PCR: A Practical Approach, M. MacPherson et al., IRL Press at Oxford University Press (1991). All processes of producing replicate copies of a polynucleotide, such as PCR or gene cloning, are collectively referred to herein as "replication." A primer can also be used as a probe in hybridization reactions, such as Southern or Northern blot analyses (Sambrook et al., Molecular Cloning: A Laboratory Manual, 2nd edition (1989)).

As used herein, "expression" refers to the process by which DNA is transcribed into mRNA and/or the process by which the transcribed mRNA is subsequently translated into peptides, polypeptides or proteins. If the polynucleotide is derived from genomic DNA, expression may include splicing of the mRNA in a eukaryotic cell.

"Differentially expressed" as applied to a gene, refers to the differential production of the mRNA transcribed and/or translated from the gene or the protein product encoded by the gene. A differentially expressed gene may be overexpressed or underexpressed as compared to the expression level of a normal or control cell.

As used herein, overexpression is an increase in gene expression and generally is at least 1.25 fold or, alternatively, at least 1.5 fold or, alternatively, at least 2 fold, or alternatively, at least 3 fold or alternatively, at least 4 fold expression over that detected in a normal or control counterpart cell or tissue. As used herein, underexpression, is a reduction of gene expression and generally is at least 1.25 fold, or alternatively, at least 1.5 fold, or alternatively, at least 2 fold or alternatively, at least 3 fold or alternatively, at least 4 fold expression under that detected in a normal or control counterpart cell or tissue. The term "differentially expressed" also refers to where expression in a cancer cell or cancerous tissue is detected but expression in a control cell or normal tissue (e.g. non cancerous cell or tissue) is undetectable.

A "gene expression profile" or "gene signature" refers to a pattern of expression of at least one biomarker that recurs in multiple samples and reflects a property shared by those samples, such as mutation, response to a particular treatment, or activation of a particular biological process or pathway in the cells. A gene expression profile differentiates between samples that share that common property and those that do not with better accuracy than would likely be achieved by assigning the samples to the two groups at random. A gene expression profile may be used to predict whether samples of unknown status share that common property or not. Some variation between the biomarker(s) and the typical profile is to be expected, but the overall similarity of biomarker(s) to the typical profile is such that it is statistically unlikely that the similarity would be observed by chance in samples not sharing the common property that the biomarker(s) reflects.

The term "cDNA" refers to complementary DNA, i.e. mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Exemplary vectors for libraries include bacteriophage (also known as "phage"), viruses that infect bacteria, for example, lambda phage. The library can then be probed for the specific cDNA (and thus mRNA) of interest.

As used herein, "solid phase support" or "solid support," used interchangeably, is not limited to a specific type of support. Rather a large number of supports are available and are known to one of ordinary skill in the art. Solid phase supports include silica gels, resins, derivatized plastic films, glass beads, plastic beads, alumina gels, microarrays, and chips. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories), polyHIPE(R)™ resin (obtained from Aminotech, Canada), polyamide resin (obtained from Peninsula Laboratories), polystyrene resin grafted with polyethylene glycol (TentaGelR™, Rapp Polymere, Tubingen, Germany), or polydimethylacrylamide resin (obtained from Milligen/Biosearch, California).

A polynucleotide also can be attached to a solid support for use in high throughput screening assays. PCT WO 97/10365, for example, discloses the construction of high density oligonucleotide chips. See also, U.S. Pat. Nos. 5,405,783; 5,412,087 and 5,445,934. Using this method, the probes are synthesized on a derivatized glass surface to form chip arrays. Photoprotected nucleoside phosphoramidites are coupled to the glass surface, selectively deprotected by photolysis through a photolithographic mask and reacted with a second protected nucleoside phosphoramidite. The coupling/deprotection process is repeated until the desired probe is complete.

As an example, transcriptional activity can be assessed by measuring levels of messenger RNA using a gene chip such as the Affymetrix® HG-U133-Plus-2 GeneChips (Affymetrix, Santa Clara, Calif.). High-throughput, real-time quantitation of RNA of a large number of genes of interest thus becomes possible in a reproducible system.

The terms "stringent hybridization conditions" refers to conditions under which a nucleic acid probe will specifically hybridize to its target subsequence, and to no other sequences. The conditions determining the stringency of hybridization include: temperature, ionic strength, and the concentration of denaturing agents such as formamide. Varying one of these factors may influence another factor and one of skill in the art will appreciate changes in the conditions to maintain the desired level of stringency. An example of a highly stringent hybridization is: 0.015M sodium chloride, 0.0015M sodium citrate at 65-68° C. or 0.015M sodium chloride, 0.0015M sodium citrate, and 50% formamide at 42° C. An example of a "moderately stringent" hybridization is the conditions of: 0.015M sodium chloride, 0.0015M sodium citrate at 50-65° C. or 0.015M sodium chloride, 0.0015M sodium citrate, and 20% formamide at 37-50° C. The moderately stringent conditions are used when a moderate amount of nucleic acid mismatch is desired. One of skill in the art will appreciate that washing is part of the hybridization conditions. For example, washing conditions can include 02.X-0.1×SSC/0.1% SDS and temperatures from 42-68° C., wherein increasing temperature increases the stringency of the wash conditions.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Gene expression" or alternatively a "gene product" refers to the nucleic acids or amino acids (e.g., peptide or polypeptide) generated when a gene is transcribed and translated.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs) and locked nucleic acids (LNAs). Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260:2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The terms "subject," "patient," and "individual" interchangeably refer to a mammal, for example, a human or a non-human primate mammal. The mammal can also be a laboratory mammal, e.g., mouse, rat, rabbit, hamster. In some embodiments, the mammal can be an agricultural mammal (e.g., equine, ovine, bovine, porcine, camelid) or domestic mammal (e.g., canine, feline).

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Activity can be assessed, e.g., using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the terms "neoplastic cells," "neoplastic disease," "neoplasia," "tumor," "tumor cells," "cancer," and "cancer cells," (used interchangeably) refer to cells which exhibit relatively autonomous growth, so that they exhibit an aberrant growth phenotype characterized by a significant loss of control of cell proliferation (i.e., deregulated cell division). Neoplastic cells can be malignant or benign. A "metastatic cell or tissue" means that the cell can invade and destroy neighboring body structures.

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of a disease or disorder.

The terms "therapeutically acceptable amount" or "therapeutically effective dose" interchangeably refer to an amount sufficient to effect the desired result (i.e., a reduction in tumor size, inhibition or prevention of tumor growth, inhibition or prevention of metastasis). In some embodiments, a therapeutically acceptable amount does not induce or cause undesirable side effects. A therapeutically acceptable amount can be determined by first administering a low dose, and then incrementally increasing that dose until the desired effect is achieved. In some embodiments, a "prophylactically effective dosage," and a "therapeutically effective dosage," of a UBC antagonist can prevent the onset of, or result in a decrease in severity of, respectively, disease symptoms, including symptoms associated with cancer and cancer treatment.

The term "co-administer" refers to the simultaneous presence of two (or more) active agents in an individual. Active agents that are co-administered can be concurrently or sequentially delivered.

As used herein, the phrase "consisting essentially of" refers to the genera or species of active pharmaceutical agents included in a method or composition, as well as any inactive carrier or excipients for the intended purpose of the methods or compositions. In some embodiments, the phrase "consisting essentially of" expressly excludes the inclusion of one or more additional active agents other than a UBC antagonist. In some embodiments, the phrase "consisting essentially of" expressly excludes the inclusion of more additional active agents other than a UBC antagonist and a second co-administered agent.

The terms "a," "an," and "the" include plural referents, unless the context clearly indicates otherwise.

DETAILED DESCRIPTION

Determining the Expression Level of a Ubiquitin Gene Product

Some embodiments disclosed herein provide methods of determining the expression level of a ubiquitin B (UBB) gene product and/or the expression level of a ubiquitin C (UBC) gene product. A gene product refers to a transcription and/or translation product from a gene, such as a UBB gene or a UBC gene, for example, mRNA, protein, etc. As used herein, the UBB gene refers to the human UBB gene, whose protein sequence has UniProt accession number POCG47; and the UBC gene, as used herein, refers to the human UBC gene, whose protein sequence has UniProt accession numbers POCG48. The UBB genomic sequence has Ensembl Reference Sequence: ENSG00000170315.13; its mRNAs result from a variety of splice forms (i.e., transcript variants), including NCBI Reference numbers NM 018955.3, NM_001281716.1, NM_001281717.1, NM 001281718.1, and NM_001281719.1. The UBC genomic sequence has Ensembl Reference Sequence: ENSG00000150991.14, it's mRNA has NCBI Reference number NM 021009.6.

A variety of assays are known in the art to determine the expression level of a UBB and/or UBC gene product. Detection of UBB and/or UBC gene expression can be by any appropriate method, including for example, detecting the quantity of mRNA transcribed from the gene or the quantity of cDNA produced from the reverse transcription of the mRNA transcribed from the gene or the quantity of the polypeptide or protein encoded by the gene. These methods can be performed on a sample by sample basis or modified for high throughput analysis. For example, using Affymetrix™ U133 microarray chips.

The expression level of a UBB and/or UBC gene product can be determined using a variety of reagents that specifically binds to a UBB and/or a UBC gene or product thereof. For example, a probe or a primer that hybridizes to the UBB and/or UBC gene, such as genomic DNA, or a gene product thereof, such as mRNA or cDNA, or an antibody that specifically bind to the UBB and/or UBC gene product, such as a protein, can be used to determine the expression level of the UBB and/or UBC gene product. In some embodiments, the probe or primer can comprise an oligonucleotide sequence that is complementary to the UBB and/or UBC gene product. In some embodiments, the probe or primer can comprise an oligonucleotide sequence that is at least 80%, at least 90%, at least 95%, at least 98%, at least 99%, or 100% homologous to the UBB and/or UBC gene product.

In some embodiments, the expression level of a UBB and/or UBC gene product can be determined by contacting a sample from a subject with a reagent that specifically binds to a UBB and/or UBC gene or product thereof to form a binding complex; and measuring the amount of the binding complex(es). In some embodiments, the reagent is a nucleic acid molecule. In some embodiments, the reagent is an antibody.

A variety of techniques are available in the art for protein analysis. They include but are not limited to radioimmunoassays, ELISA (enzyme linked immunosorbent assays), "sandwich" immunoassays, immunoradiometric assays, in situ immunoassays (using e.g., colloidal gold, enzyme or radioisotope labels), Western blot analysis, immunoprecipitation assays, immunofluorescent assays, flow cytometry, immunohistochemistry, HPLC, mass spectrometry, confocal microscopy, enzymatic assays, surface plasmon resonance and PAGE-SDS.

In one aspect, the level of UBB and/or UBC gene expression is determined and quantitated by hybridization to a probe that specifically hybridizes to the UBB and/or UBC gene, such as genomic DNA, or a gene product thereof, such as an mRNA or cDNA. The probes also can be attached to a solid support for use in high throughput screening assays using methods known in the art. WO 97/10365 and U.S. Pat. Nos. 5,405,783, 5,412,087 and 5,445,934, for example, disclose the construction of high density oligonucleotide chips which can contain one or more of the sequences disclosed herein. Using the methods disclosed in U.S. Pat. Nos. 5,405,783, 5,412,087 and 5,445,934, the probes of this invention are synthesized on a derivatized glass surface. Photoprotected nucleoside phosphoramidites are coupled to the glass surface, selectively deprotected by photolysis through a photolithographic mask, and reacted with a second protected nucleoside phosphoramidite. The coupling/deprotection process is repeated until the desired probe is complete.

In one aspect, the expression level of a UBB and/or UBC gene is determined through exposure of a nucleic acid sample to the probe-modified chip. Extracted nucleic acid is labeled, for example, with a fluorescent tag, preferably during an amplification step. Hybridization of the labeled sample is performed at an appropriate stringency level. The degree of probe-nucleic acid hybridization is quantitatively measured using a detection device. See U.S. Pat. Nos. 5,578,832 and 5,631,734.

Alternatively any one of gene copy number, transcription, or translation can be determined using known techniques. For example, an amplification method such as PCR may be useful. General procedures for PCR are taught in MacPherson et al., PCR: A Practical Approach, (IRL Press at Oxford University Press (1991)). However, PCR conditions used for each application reaction are empirically determined. A number of parameters influence the success of a reaction. Among them are annealing temperature and time, extension time, $Mg^{2+}$ and/or ATP concentration, pH, and the relative concentration of primers, templates, and deoxyribonucleotides. After amplification, the resulting DNA fragments can be detected by agarose gel electrophoresis followed by visualization with ethidium bromide staining and ultraviolet illumination.

In one embodiment, the hybridized nucleic acids are detected by detecting one or more labels attached to the sample nucleic acids. The labels can be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, poly A, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present disclosure include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., 3FL 1251, 35S, 14C, or 32P) enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Detection of labels is well known to those of skill in the art. Thus, for example, radiolabels may be detected using photographic film or scintillation counters, fluorescent markers may be detected using a photodetector to detect emitted light.

Enzymatic labels are typically detected by providing the enzyme with a substrate and detecting the reaction product produced by the action of the enzyme on the substrate, and calorimetric labels are detected by simply visualizing the coloured label.

The detectable label may be added to the target (sample) nucleic acid(s) prior to, or after the hybridization, such as described in WO 97/10365. These detectable labels are directly attached to or incorporated into the target (sample) nucleic acid prior to hybridization. In contrast, "indirect labels" are joined to the hybrid duplex after hybridization. Generally, the indirect label is attached to a binding moiety that has been attached to the target nucleic acid prior to the hybridization. For example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization with Nucleic Acid Probes, P. Tijssen, ed. Elsevier, N.Y. (1993).

A reduction in the expression level of the UBB gene product can be caused by a variety of reasons, for example, by a reduced copy number of the UBB gene, by a mutation in the UBB gene that either reduces the transcription/translation of the UBB gene or results in destabilization of the UBB gene product, by a change in DNA methylation that leads to reduced UBB promoter activity, etc. Therefore, in some embodiments, the copy number of the UBB gene, the mutation in the UBB gene, and/or the methylation pattern of the UBB gene may be assayed for the detection of reduced expression level of the UBB gene product in a patient sample. In some embodiments, the expression level of the UBB gene product and the expression level of the UBC gene product can be both measured and compared, for example, to calculate a ratio between the expression level of the UBC gene product and the expression level of the UBB gene product.

In some embodiments, the copy number of the UBB gene, the mutation in the UBB gene, and/or the methylation pattern of the UBB gene may be assayed for the detection of reduced expression level of the UBB gene product in a patient sample. UBB mutations when translated into proteins can be detected by specific antibodies. Mutations in the UBB protein can change the antigenicity of the UBB protein, so that an antibody raised against a UBB mutant antigen (e.g. a specific peptide containing a mutation) will specifically bind the mutant UBB and not recognize the wild-type.

Mutations in the UBB gene and/or copy number of the UBB gene can also be determined by examining protein expression or the protein product of the UBB gene. Determining the protein level involves measuring the amount of any immunospecific binding that occurs between an antibody that selectively recognizes and binds to the UBB polypeptide in a sample obtained from a patient and comparing this to the amount of immunospecific binding the UBB polypeptide in a control sample. The amount of protein expression of the UBB can be increased or reduced when compared with control expression.

Antibodies directed against UBB can be useful in the detection of cancer and the detection of mutated forms of UBB. For example, provided herein are methods of detecting UBB+1, as a result of a frameshift mutation near the very end of the UBB mRNA and leads to the translation of a UBB+1 variant that has a G76Y mutation and 19 additional AAs. UBB+1 is often associated with neurodegenerative diseases and acts by inhibiting proteosomal degradation (Chojnacki, et al., 2016). Antibodies can be generated which recognize and specifically bind only a specific mutant of UBB such as the UBB+1 variant and do not bind (or weakly bind) to wild type UBB. These antibodies would be useful in determining which specific mutation such as the UBB+1 variant was present and also in quantifying the level of UBB protein. For example, an antibody can be directed against a functional domain of a UBB protein, such as the ubiquitin-like domain. An antibody that recognizes this amino acid change and does not specifically bind to wild type UBB could identify the specific mutation in tissue sections and also the protein levels by Western blotting. Such antibodies can be generated against a UBB mutation or a translation variant such as the UBB+1 variant by using peptides containing the specific UBB mutation of interest.

A cancer cell believed to contain a UBB mutation can be lysed and Western blotting performed to detect the amount of UBB mutant protein such as the UBB+1 variant, using a cell containing wild type UBB as a control.

The detection of UBB mutations can be done by any number of ways for nucleic acid detection, for example: DNA sequencing, PCR based methods, including RT-PCR, microarray analysis, Southern blotting, Northern blotting, Next Generation Sequencing, and dip stick analysis.

Methods of detecting UBB mutations by hybridization are provided. The method comprises identifying a UBB mutation in a sample by contacting nucleic acid from the sample with a nucleic acid probe that is capable of hybridizing to nucleic acid with a UBB mutation or fragment thereof and detecting the hybridization. The nucleic acid probe is detectably labeled with a label such as a radioisotope, a fluorescent agent or a chromogenic agent. Radioisotopes can include without limitation; 3H, 32P, 33P and 35S etc. Fluorescent agents can include without limitation: FITC, texas red, rhodamine, etc.

The probe used in detection that is capable of hybridizing to nucleic acid with a UBB mutation can be from about 8 nucleotides to about 100 nucleotides, from about 10 nucleotides to about 75 nucleotides, from about 15 nucleotides to about 50 nucleotides, or about 20 to about 30 nucleotides. The probe or probes can be provided in a kit, which comprise at least one oligonucleotide probe that hybridizes to or hybridizes adjacent to a UBB mutation. The kit can also provide instructions for analysis of patient cancer samples that can contain a UBB mutation, and which UBB mutations indicate that the patient is sensitive or insensitive to treatment with a UBC antagonist.

Single stranded conformational polymorphism (SSCP) can also be used to detect UBB mutations. This technique is well described in Orita et al., PNAS 1989, 86:2766-2770.

The expression level of a UBB and/or UBC gene product can be measured using a sample of the patient. In some embodiments, the sample can be a blood sample, a urine sample, a tissue sample, a biopsy sample, or any combination thereof. The sample can comprise a single cell, or a plurality of cells. For example, the sample can comprise a cancer sample, or a non-cancer sample. A cancer sample can comprise one or more cancer cells.

Methods of Predicting or Prognosing Responsiveness to a Treatment

Some embodiments disclosed herein provide methods of predicting or prognosing responsiveness to a treatment by a cancer patient, wherein the treatment comprises administering a ubiquitin C (UBC) antagonist to the cancer patient. In some embodiments, the responsiveness of the cancer patient to the treatment can be determined by the expression level of a UBB gene product and/or the expression level of a UBC gene product, and/or the ratio between the expression level of a UBB gene product and the expression level of a UBC gene product determined by the compositions and methods as disclosed herein. In some embodiments, the responsiveness to the treatment can be determined by the presence of a mutant UBB gene product such as the UBB+1 variant.

In some embodiments, the cancer patient having a reduced expression level of a UBB gene product is determined to be responsive to the treatment. As used herein, "a reduced expression level" refers to an expression level that is reduced in comparison to a reference expression level. For example, a reference expression level of a gene produce can be the expression level of the gene product in a normal subject or the average expression level of the gene product in a group of normal subjects, or the expression level of the gene product in a normal sample of the patient, such as a non-cancerous sample. In some embodiments, the patient can have a reduction in the expression level of the gene product that is, is about, is at least, 10%, 20%, 30%, 40%, 50%, 60%, 70%, 80%, 90%, 95%, 98%, 99%, 100%, or a range between any two of the above values. In some embodiments, the cancer patient having a ratio of an expression level of a UBC gene product to an expression level of a UBB gene product that is greater than a reference ratio is determined to be responsive to the treatment. In some embodiments, the reference ratio between the expression level of a UBC gene product to the expression level of a UBB gene product can be the ratio between the expression level of a UBC gene product to the expression level of a UBB gene product in a normal subject or the average ratio between the expression level of a UBC gene product to the expression level of a UBB gene product in a group of normal subject, or the ratio between the expression level of a UBC gene product to the expression level of a UBB gene product in a normal sample of the patient, such as a non-cancerous sample. In some embodiments, the patient can have a ratio between the expression level of a UBC gene product to the expression level of a UBB gene product that is, is about, is at least, 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00, 3.00, 4.00, 5.00, 6.00, 7.00, 8.00, 9.00, 10.00, or a range between any two of the above values. In some embodiments, the patient can have a ratio between the expression level of a UBC gene product to the expression level of a UBB gene product that is at least 1.25.

Cancer

A variety of cancers can be treated by the methods and compositions disclosed herein. In some embodiments, the cancer is characterized by a reduced expression level of a UBB gene product, and/or a ratio of an expression level of a UBC gene product to an expression level of a UBB gene product that is greater than 1.25. In some embodiments, the cancer is characterized by the expression of a mutant UBB protein such as the UBB+1 variant. In some embodiments, the cancer is a solid tumor. In some embodiments, the cancer is a hematopoietic cancer. In some embodiments, the cancer is a tumor of the female reproductive tract, such as uterine sarcoma, endometrial carcinoma, or ovarian adenocarcinoma.

The methods and compositions disclosed herein find use in treatment, amelioration or prophylaxis of cancer. In one aspect, the disclosure provides methods of treatment of cancer in an individual in need thereof, comprising administering to the individual a therapeutically effective amount of a UBC antagonist, as described herein. In some embodiment a UBC antagonist is provided for use as a therapeutic agent in the treatment or prophylaxis of cancer in an individual. In a further aspect, the disclosure provides a composition comprising such a UBC antagonist for use in treating or ameliorating cancer in an individual in need thereof.

Conditions subject to treatment include various cancer indications. For therapeutic purposes, an individual was diagnosed with cancer. For preventative or prophylactic purposes, an individual may be in remission from cancer or may anticipate future onset. In some embodiments, the patient has cancer, is suspected of having cancer, or is in remission from cancer. Cancers subject to treatment with a UBC antagonist may derive benefit from inducing a DNA damage response (DDR), as described herein. Cancer indications subject to treatment include without limitation: uterine sarcoma, endometrial carcinoma, or ovarian adenocarcinoma.

Methods of Treating, Ameliorating, or Preventing Cancer

Some embodiments disclosed herein provide methods of treating, ameliorating, or preventing cancer in a patient, comprising: (a) identifying a patient having cancer with a reduced expression level of a ubiquitin B (UBB) gene product or a patient having cancer with a ratio of an expression level of a ubiquitin C (UBC) gene product to an expression level of a ubiquitin B (UBB) gene product that is greater than 1.25 or a patient having cancer with expression of a mutant UBB protein such as the UBB+1 variant; and (b) administrating to the patient a ubiquitin C (UBC) antagonist. In some embodiments, the UBC antagonist is an anti-sense nucleic acid, a short hairpin RNA (shRNA) or a short inhibitory RNA (siRNA). In some embodiments, the shRNA targets the nucleic acid sequence set forth in SEQ ID NO:1, In some embodiments, the UBC antagonist is a compound. In some embodiments, the UBC antagonist is a small molecule compound. In some embodiments, the small molecule compound specifically binds to the UBC mRNA. For therapeutic purposes, a patient is diagnosed with cancer. For preventative or prophylactic purposes, a patient may be in remission from cancer or may anticipate future onset. In some embodiments, the patient has cancer, is suspected of having cancer, or is in remission from cancer.

In some embodiments, the methods disclosed herein can be used to treat a patient having cancer with a reduced expression level of a UBB gene product or a mutant UBB protein such as the UBB+1 variant. As used herein, "a reduced expression level" refers to an expression level that is reduced in comparison to a reference expression level. For example, a reference expression level of a gene produce can be the expression level of the gene product in a normal subject or the average expression level of the gene product in a group of normal subject, or the expression level of the gene product in a normal sample of the patient, such as a non-cancerous sample. In some embodiments, the patient can have cancer with a reduction in the expression level of the gene product that is, is about, is at least, 10%, 20%, 30%, 40%, 50%, 60%, 70%, 80%, 90%, 95%, 98%, 99%, 100%, or a range between any two of the above values. In some embodiments, the methods disclosed herein can be used to treat a patient having cancer with a ratio of an expression level of a UBC gene product to an expression level of a UBB gene product that is greater than a reference ratio. In some embodiments, the reference ratio between the expression level of a UBC gene product to the expression level of a UBB gene product can be the ratio between the expression level of a UBC gene product to the expression level of a UBB gene product in a normal subject or the average ratio between the expression level of a UBC gene product to the expression level of a UBB gene product in a group of normal subject, or the ratio between the expression level of a UBC gene product to the expression level of a UBB gene product in a normal sample of the patient, such as a non-cancerous sample. In some embodiments, the patient can have cancer with a ratio between the expression level of a UBC gene product to the expression level of a UBB gene product that is, is about, is at least, 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00, 3.00, 4.00, 5.00, 6.00, 7.00, 8.00, 9.00, 10.00, or a range between any two of the above values. In some embodiments, the patient can have cancer with a ratio between the expression level of a UBC gene product to the expression level of a UBB gene product that is at least 1.25.

The UBC antagonist can be administered in single or divided doses. The UBC antagonist is usually administered on multiple occasions. Intervals between single dosages can be weekly, bi-weekly, monthly or yearly, as needed or desired. Intervals can also be irregular as indicated by measuring blood levels of the UBC antagonist in the patient. In some methods, dosage is adjusted to achieve a plasma UBC antagonist concentration of 1-1000 µg/ml and in some methods 25-300 µg/ml. Alternatively, the UBC antagonist can be administered as a sustained release formulation, in which case less frequent administration is required. Dosage and frequency vary depending on the half-life of the UBC antagonist in the patient. In general for prophylactic applications, a relatively low dosage is administered at relatively infrequent intervals over a long period of time. Some patients continue to receive treatment for the duration of their lives. In general for therapeutic applications, a relatively high dosage in relatively short intervals is sometimes required until progression of the disease is reduced or terminated, and preferably until the patient shows partial or complete amelioration of symptoms of disease. Thereafter, a patient may be administered a prophylactic regime.

Methods of Sensitizing a Cancer Patient for Chemotherapy

Some embodiments disclosed herein provide methods of sensitizing a patient having cancer for a chemotherapy treatment comprising administering to the patient a ubiquitin C (UBC) antagonist.

In some embodiments, the chemotherapy treatment causes a DNA damage response (DDR) in the patient. In some embodiments, the chemotherapy treatment comprises administering an alkylating agent, an antimetabolite, an anti-microtubule agent, a topoisomerase inhibitor, a cytotoxic antibiotic, or any combination thereof. In some embodiments, the alkylating agent may be mechlorethamine, cyclophosphamide, melphalan, chlorambucil, ifosfamide, busulfan, N-Nitroso-N-methylurea (MNU), carmustine (BCNU), lomustine (CCNU), semustine (MeCCNU), fotemustine, streptozotocin, dacarbazine, mitozolomide, temozolomide, thiotepa, mytomycin, diaziquone (AZQ), cisplatin, carboplatin oxaliplatin, procarbazine, hexamethylmelamine, or a derivative thereof. In some embodiments, the antimetabolite may be an anti-folate such as methotrexate or pemetrexed, a fluoropyrimidine such as fluorouracil or capecitabine, a deoxynucleoside analogue such as cytarabine, gemcitabine, decitabine, Vidaza, fludarabine, nelarabine, cladribine, clofarabine or pentostatin, a thiopurine such as thioguanine or mercaptopurine, or a derivative thereof. In some embodiments, the anti-microtubule agent may be a *vinca* alkaloid such as vincristine, vinblastine, vinorelbine, vindesine, or vinflunine, a taxane such as paclitaxel or docetaxel, an antineoplastic lignan such as Podophyllotoxin, etoposide or teniposide, or a derivative thereof. In some embodiments, the topoisomerase inhibitor may be a topoisomerase I inhibitor such as irinotecan or topotecan, a topoisomerase II inhibitor such as etoposide, doxorubicin, mitoxantrone, teniposide, novobiocin, merbarone, or aclarubicin, or a derivative thereof. In some embodiments, the cytotoxic antibiotic may be an anthracycline such as doxorubicin, daunorubicin, epirubicin, idarubicin, pirarubicin, aclarubicin, mitoxantrone, a bleomycin, mitomycin C, actinomycin, or a derivative thereof. In some embodiments, the chemotherapy treatment comprises administering cisplatin to the patient.

In some embodiments, the UBC antagonist is an antisense nucleic acid such as DNA, RNA, LNA, PNA, etc., a short hairpin RNA (shRNA) or a short inhibitory RNA (siRNA). In some embodiments, the shRNA targets the nucleic acid sequence set forth in SEQ ID NO: 1, In some embodiments, the UBC antagonist is a compound. In some embodiments, the UBC antagonist is a small molecule compound. In some embodiments, the small molecule compounds specifically bind to the UBC mRNA.

Pharmaceutical Compositions

Some embodiment disclosed herein provide pharmaceutical compositions for treating cancer in a patient comprising a therapeutically effective amount of a ubiquitin C (UBC) antagonist and an excipient. In some embodiments, the pharmaceutical compositions disclosed herein may be used in treating cancer in a patient. Excipients, such as pharmaceutically acceptable carriers, may enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

As used herein a "UBC antagonist" refers to a molecule that reduces or inhibits the activity of a UBC gene product, by either reducing the expression of the UBC gene product or interfering with its activity in the cell, such as being recognized by one of the ubiquitin-activating enzymes (E1s), ubiquitin-conjugating enzymes (E2s), and ubiquitin ligase enzymes (E3s); or forming ubiquitin chains. In some embodiments, the UBC antagonist is a compound, such as a small molecule compound. In some embodiments, the small molecule compound specifically binds to the UBC mRNA. In some embodiments, the UBC antagonist is an anti-sense nucleic acid, an siRNA, or an shRNA. In some embodiments, the shRNA targets the nucleic acid sequence set forth in SEQ ID NO: 1.

A pharmaceutical composition of the present disclosure can be administered by a variety of methods known in the art. Route and/or mode of administration vary depending upon the desired results. It is preferred that administration be by parenteral administration (e.g., selected from any of intravenous, intramuscular, intraperitoneal, intrathecal, intraarterial, or subcutaneous), or administered proximal to the site of the target. A pharmaceutically acceptable carrier is suitable for administration by any one or more of intravenous, intramuscular, intraperitoneal, intrathecal, intraarterial, subcutaneous, intranasal, inhalational, spinal or epidermal administration (e.g., by injection). Depending on the route of administration, an active compound, e.g., a UBC antagonist, may be coated in a material to protect the compound from the action of acids and other natural conditions that may inactivate the compound. In some embodiments the pharmaceutical composition is formulated for intravenous administration. In some embodiments the pharmaceutical composition is formulation for subcutaneous administration. A UBC antagonist, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

In some embodiments, a pharmaceutical composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. In certain embodiments compositions can be prepared for storage in a lyophilized form using appropriate excipients (e.g., sucrose).

Pharmaceutical compositions can be prepared in accordance with methods well known and routinely practiced in the art. Pharmaceutically acceptable carriers are determined in part by the particular composition being administered, as well as by the particular method used to administer the composition. Accordingly, there is a wide variety of suitable formulations of pharmaceutical compositions. Applicable methods for formulating a UBC antagonist and determining appropriate dosing and scheduling can be found, for example, in *Remington: The Science and Practice of Pharmacy*, 21$^{st}$ Ed., University of the Sciences in Philadelphia, Eds., Lippincott Williams & Wilkins (2005); and in *Martindale: The Complete Drug Reference*, Sweetman, 2005, London: Pharmaceutical Press., and in Martindale, *Martindale: The Extra Pharmacopoeia*, 31st Edition., 1996, Amer Pharmaceutical Assn, and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of a UBC antagonist is employed in the pharmaceutical compositions. A UBC antagonist is formulated into pharmaceutically acceptable dosage form by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of active ingredients in the pharmaceutical compositions can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Starting doses of a UBC antagonist employed in the pharmaceutical composition at levels lower than that required to achieve the desired therapeutic effect and gradually increase the dosage until the desired effect is achieved. In general, effective doses of the compositions vary depending upon many different factors, including the specific disease or condition to be treated, means of administration, target site, physiological state of the patient, whether a patient is human or an animal, other medications administered, and whether treatment is prophylactic or therapeutic. Treatment dosages typically require titration to optimize safety and efficacy. For administration with a UBC antagonist, dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. Dosing can be daily, weekly, bi-weekly, monthly, or more or less often, as needed or desired. An exemplary treatment regime entails administration once weekly, once per every two weeks or once a month or once every 3 to 6 months.

Co-Administration with a Second Agent

In some embodiments, the pharmaceutical compositions disclosed herein may be used in a combination therapy to a cancer patient in need thereof. The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating cancer by administering to a subject in need thereof a UBC antagonist in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); nilotinib (Tasigna®); Regorafenib (Stivarga®) and Imatinib or Imatinib mesylate (Gilvec® and Gleevec®).

Epidermal growth factor receptor (EGFR) inhibitors include but are not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or $p^1 85$) inhibitors include but are not limited to, Trastuzumab (Herceptin®); Pertuzumab (Omnitarg®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,11-f][1,2,4]triazin-5-yl)methyl)piperidin-3-ol (BMS-690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-m-ethylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and B1836845. See e.g., Yee, JNCI, 104; 975 (2012) for review.

In another aspect, the present disclosure provides a method of treating cancer by administering to a subject in need thereof a UBC antagonist in combination with one or more FGF receptor downstream signaling pathway inhibitors, including but not limited to, MEK inhibitors, Braf inhibitors, PI3K/Akt inhibitors, SHP2 inhibitors, and also mTor inhibitors.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

mTor inhibitors include but are not limited to, Temsirolimus (Torisel®); Ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d]pyrimidin-7-yl)}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-("L-arginylglycyl-L-α-aspartylL-serine" disclosed as SEQ ID NO: 24), inner salt (SF1126, CAS 936487-67-1).

In yet another aspect, the present disclosure provides a method of treating cancer by administering to a subject in need thereof a UBC antagonist in combination with one or more pro-apoptotics, including but not limited to, IAP inhibitors, Bcl2 inhibitors, MCl1 inhibitors, Trail agents, Chk inhibitors.

For examples, IAP inhibitors include but are not limited to, NVP-LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386); Tetrocarcin A; Antimycin; Gossypol ((-)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (-)-Gossypol acetic acid (AT-101); 4-[4-[(4'-Chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS 1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7,4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3 (2H)-dione (SB-218078, CAS 135897-06-2); and TAT-S216A (Sha et al., Mol. Cancer. Ther 2007; 6(1):147-153), and CBP501.

In one aspect, the present disclosure provides a method of treating cancer by administering to a subject in need thereof a UBC antagonist in combination with one or more FGFR inhibitors. For example, FGFR inhibitors include but are not limited to, Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Vargatef (BIBF1120, CAS 928326-83-4); Dovitinib dilactic acid (TKI258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and (PD173074, CAS 219580-11-7). In a specific aspect, the present disclosure provides a method of treating cancer by administering to a subject in need thereof an antibody drug conjugate in combination with an FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazin 1-yl)-1H-benzo[d]imidazole-2-yl)quinolin-2(1H)-one (also known as dovitinib or TKI-258). AZD4547 (Gavine et al., 2012, Cancer Research 72, 2045-56, N-[5-[2-(3,5-Dimethoxyphenyl)ethyl]-2H-pyrazol-3-yl]-4-(3R, 5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-({4-[(4-methylpiperazin-1-yl)methyl]-3-(trifluoromethyl)phenyl}benzamide, CAS 943319-70-8).

The UBC antagonist can also be administered in combination with an immune checkpoint molecule. In one embodiment, the UBC antagonist can be administered in combination with an inhibitor of an immune checkpoint molecule chosen from one or more of PD-1, PD-L1, PD-L2, TIM3, CTLA-4, LAG-3, CEACAM-1, CEACAM-5, VISTA, BTLA, TIGIT, LAIR1, CD160, 2B4 or TGFR In one embodiment, the immune checkpoint molecule is an anti-PD-1 inhibitor, wherein the anti-PD-1 antibody is chosen from Nivolumab, Pembrolizumab or Pidilizumab. In some embodiments, the anti-PD-1 antibody molecule is Nivolumab. Alternative names for Nivolumab include MDX-1106, MDX-1106-04, ONO-4538, or BMS-936558. In some embodiments, the anti-PD-1 antibody is Nivolumab (CAS Registry Number: 946414-94-4). Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and WO2006/121168.

In some embodiments, the anti-PD-1 antibody molecule is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) New England Journal of Medicine 369 (2): 134-44, U.S. Pat. No. 8,354,509 and WO2009/114335.

In some embodiments, the anti-PD-1 antibody molecule is Pidilizumab. Pidilizumab (CT-011; Cure Tech) is a humanized IgG1k monoclonal antibody that binds to PD1. Pidilizumab and other humanized anti-PD-1 monoclonal antibodies are disclosed in WO2009/101611.

Other anti-PD1 antibody molecules include AMP 514 (Amplimmune) and, e.g., anti-PD1 antibodies disclosed in U.S. Pat. No. 8,609,089, US 2010/028330, and/or US 2012/0114649 and US2016/0108123.

In some embodiments, the UBC antagonist can be administered with the anti-Tim3 antibody disclosed in US2015/0218274. In other embodiments, the UBC antagonist can be administered with the anti-PD-L1 antibody disclosed in US2016/0108123, Durvalumab® (MEDI4736), Atezolizumab® (MPDL3280A) or Avelumab®.

Articles of Manufacture/Kits

In some aspects a UBC antagonist is provided in an article of manufacture (i.e., a kit). A provided UBC antagonist is generally in a vial or a container. Thus, an article of manufacture comprises a container and a label or package insert, on or associated with the container. Suitable containers include, for example, a bottle, vial, syringe, solution bag, etc. As appropriate, the UBC antagonist can be in liquid or dried (e.g., lyophilized) form. The container holds a composition which, by itself or combined with another composition, is effective for preparing a composition for treating, preventing and/or ameliorating cancer. The label or package insert indicates the composition is used for treating, preventing and/or ameliorating cancer. Articles of manufacture (kits) comprising a UBC antagonist, as described herein, optionally contain one or more additional agent. In some embodiments, an article of manufacture (kit) contains a UBC antagonist and a pharmaceutically acceptable diluent. In some embodiments a UBC antagonist is provided in an article of manufacture (kit) with one or more additional active agent in the same formulation (e.g., as mixtures). In some embodiments a UBC antagonist is provided in an article of manufacture (kit) with a second or third agent in separate formulations (e.g., in separate containers). In certain embodiments an article of manufacture (kit) contains aliquots of a UBC antagonist wherein the aliquot provides for one or more doses. In some embodiments aliquots for multiple administrations are provided, wherein doses are uniform or varied. In particular embodiments varied dosing regimens are escalating or decreasing, as appropriate. In some embodiments dosages of a UBC antagonist and a second agent are independently uniform or independently varying. In certain embodiments, an article of manufacture (kit) comprises an additional agent such as an anti-cancer agent or immune checkpoint molecule. Selection of one or more additional agent will depend on the dosage, delivery, and disease condition to be treated.

In some embodiments, an article of manufacture (kit) contains a reagent for determining the expression level of a UBB gene product and/or a UBC gene product. In some embodiments, the reagent comprises a nucleic acid molecule, such as a probe or a primer, which specifically binds to a UBB gene product and/or a UBC gene product. In some embodiments, the reagent comprises an antibody that specifically binds to a UBB gene product and/or a UBC gene product.

EXAMPLES

We continued to look for stratification-based opportunities that could serve as the starting points for a next generation of treatment options using the TCGA dataset. This approach led to the identification of a recurrent alteration in the expression of the ubiquitin gene UBB, which is silenced in a significant subset of ovarian cancer patients. This alteration is not seen in normal ovarian tissue, suggesting that UBB silencing occurs during tumorigenesis. Several cell lines profiled as part of the Cancer Cell Line Encyclopedia (CCLE) also contain UBB in a transcriptionally repressed state, enabling us to assess the therapeutic value of this observation.

UBB is one of two polyubiquitin genes, along with UBC, that encode multiple ubiquitin genes in a tandem, head-to-tail array (Wiborg, et al., 1985). Knockdown of UBC in the aforementioned cells led to depletion of cellular ubiquitin pools and cell death, and we showed that this effect is specific and rescuable. We confirmed the therapeutic relevance of these observations in an in vivo xenograft study.

Pan-cancer TCGA data analysis has led to the novel finding that UBB silencing, while infrequent in most cancer types, occurs in approximately 15-30% of all profiled gynecological cancers, including uterine sarcoma and endometrial cancer in addition to ovarian cancer. Our functional studies provided a basis for considering UBC as essential to the survival of cells lacking UBB expression both in vitro and in vivo. We propose that the combined loss of ubiquitin from both UBB and UBC leads to a catastrophic deficiency of ubiquitin. This synthetic lethal dependency exploits a tumor-specific deficiency in ubiquitin gene expression and establishes a targeted approach for such patients based on a lethal ubiquitin insufficiency.

We have identified a subset of ovarian cancer patients that are deficient for the expression of a gene critical for the establishment of cellular ubiquitin levels. The polyubiquitin gene UBB is transcriptionally repressed in approximately 30% of ovarian cancers leading to a dependence on the polyubiquitin gene, UBC. Inhibition of UBC is lethal in UBB-repressed cells. This synthetic lethal relationship was validated in vivo, finding robust regressions of established orthotopic ovarian tumors following inducible expression of shRNA targeting UBC. Transcriptional repression of UBB is a cancer subtype-specific alteration that occurs in a significant population of patients with cancers of the female reproductive tract, including uterine sarcoma, endometrial carcinoma, as well as ovarian adenocarcinoma, where it is associated with poor survival outcomes. The prognostic value and demonstrated efficacy established these observations as clinically relevant and defined UBC as an important target for precision medicine among ovarian cancer patients.

Methods

Cell Culture

All cell lines are described, authenticated, and profiled as part of the Novartis/Broad Institute Cancer Cell Line Encyclopedia ("CCLE") (Barretina, et al., 2012). Prior to use in these studies, all lines were re-authenticated using Affymetrix SNP 6.0 array (Asuragen) and compared to reference genomes in CCLE. Cells were tested and found to be negative for *mycoplasma* using the MycoAlert kit (Lonza, LT07). Growth of all lines was at 37° C. with 5% $CO_2$ in the corresponding media: CAL33, HMCB, and A2058 were cultured in DMEM (Gibco); DEL, HCC-44, OC316, OVCAR8, MDA-MB-231, and NCI-1299 were cultured in RPMI (Gibco); JHOM1 was cultured in DMEM:F12 (Gibco); KYSE150 was cultured in RPMI:F12 (Gibco); KS-1, AZ521, and OVK18 were cultured in EMEM (ATCC); RKO was cultured in McCoy's 5A (Gibco). During authentication, we determined that AZ521 is commonly misidentified as HuTu80; however, the cells in our study were confirmed as AZ521 against the CCLE reference. All media was supplemented with 10% Fetal Bovine Serum (FBS, Hyclone, #SH30071.03). Tet-on promoter was induced with 100 ng/ml Doxycycline (Sigma, #T7660). For colony formation assays, cells were cultured until colonies were visible by eye. Plates were then stained with crystal violet solution [0.2% w/v crystal violet (Sigma, #C0775), 4% v/v formalin (Fisher Scientific, #F79-500) in PBS solution] for 15-30 minutes and washed three times with distilled water. Plate images were visualized on the Odyssey LiCor.

mRNA Expression Level

RNA was extracted using the RNeasy Kit (Qiagen, #74181) or the TurboCapture 96 mRNA kit (Qiagen, #72251). cDNA was reverse transcribed using the High-Capacity cDNA Reverse Transcription Kit (Applied Biosystems, #4368814) or Cells-to-Ct RT reagents (Applied Biosystems, #4391852C). mRNA levels were determined by Taqman qPCR with probe sets purchased from Applied Biosystems using an ABI7900HT Fast Real-Time PCR instrument (Applied Biosystems): ATR Hs00992123_m1, UBA52 Hs03004331_g1, RPS27A Hs01923841_uH or Hs01577583_g1, UBB Hs00430290_m1, UBC Hs01871556_s1 or Hs00824723_m1, and PLK1 Hs00153444_ml. Data were normalized using an internal control gene, either GAPDH (Invitrogen, #4352934E) or beta-actin (Applied Biosystems, #Hs99999903 ml). Relative quantification of expression levels (RQ) was calculated using the $2^{-\Delta\Delta ct}$ method or relative quantitation (Schmittgen, et al., 2008). For analysis of expression in tumor tissue, multiple nodules per mouse were removed and stored in RNAlater. mRNA was extracted with Trizol and isolated using the RNeasy Kit. Samples were subject to reverse transcription and amplified by Taqman. Results were analyzed individually and subsequently combined as a group. Four to five nodules were isolated from each mouse, and two mice were included from each group. To restrict the analysis to the human cells in the sample, results were normalized to human GAPDH by the $\Delta\Delta CT$ method. UBC levels were then normalized to the shNT No Dox sample. Error is expressed as the standard deviation.

siRNA Transfection

Cells identified in the CCLE to have low or normal UBB expression were reverse transfected in 96-well plates. UBC siRNAs were purchased from either Dharmacon (J-019408-05 (GUAAGACCAUCACUCUCGA (SEQ ID NO:12)), J-019408-06 (GUGAAGACCCUGACUGGUA (SEQ ID NO:13)), J-019408-07 (AAGCAAAGAUCCAGGACAA (SEQ ID NO:14)), J-019408-08 (GUGAAGACUCUGACUGGUA (SEQ ID NO: 15))) or Qiagen (SI00754271 (GAGGTTGATCTTTGCCGGAAA (SEQ ID NO: 16)), SI00754278 (GAGGTTGATCTTTGCTGGGAA (SEQ ID NO: 17))); or designed internally (UBC-1 antisense: TCAAGTGACGATCACAGCG (SEQ ID NO:20), UBC-1 sense: CGCTGTGATCGTCACTTGA (SEQ ID NO:21); UBC-2 antisense: TTATTGAAAGGAAAGTGCA (SEQ ID NO:22), and UBC-2 sense: TGCACTTTCCTTTCAATAA (SEQ ID NO:23)). UBB siRNAs were purchased from Qiagen S103107328 (UBB-1) (TAAAGGTTTCGTTGCATGGTA (SEQ ID NO: 18)) and Dharmacon J-03382-07 (UBB-2) (UCGAAAAUGUGAAGGCCAA (SEQ ID NO:19)). Non-targeting (NT) control siRNA was purchased from Dharmacon (D-001810-01-05), and PLK1 siRNA was purchased from Qiagen (SI02223837). siRNAs were resuspended to a final stock concentration of 20 µM in nuclease-free water for all applications. For titration studies, a dilution of siRNA (OptiMEM I) was prepared at 10× final concentration. Dharmafect-1 (Dharmacon, #T-2001) was diluted 1:40 in OptiMEM I for a 1:400 final concentration. 10 µl of diluted siRNAs were arrayed into each well in 96-well plates, and 10 µl of diluted Dharmafect-1 was added to each well. Cells were trypsinized, counted, and seeded into wells at 10,000 cells in 80 µl media. Viability was assessed by adding 100 µl CellTiter-Glo (CTG) at 72 hours (Promega, #G7573); after 10 minutes of incubation and gentle agitation, Relative Light Units (RLU) were measured using the EnVision plate reader (Perkin Elmer). Replicate sets of plates from the reverse transfection were used in additional assays including colony forming assays (CFA), Incucyte assay (Essen Bioscience, Inc.)—wherein wells were scanned every 12 hours for seven days to assess confluence to generate growth curves—and mRNA detection, as described above. CFA results were reproducible using six independent UBC siRNAs.

UBB/UBC Synthetic Lethality Studies Using siUBB and siUBC

Two UBC siRNAs and two UBB siRNAs, previously established as specifically knocking down their respective target mRNAs, and a NT control siRNA were arrayed into 96-well plates in matrix format at a final concentration of 10 nM for each siRNA. OVCAR8, OC316, A2058, and HMCB cells were reverse transfected. Viability was assessed by CTG 72 hours later. mRNA levels for UBB and UBC were assessed 24 hours post-transfection.

Cell Cycle Analysis

Cells were plated into 6-well plates ($0.5 \times 10^6$ per well) as biological replicates and transfected the next day with the following siRNAs: siNT (Dhamacon D-001810-01-05), siPLK1 (Dhamacon D-003290-05), or siUBC (Dharmacon J-019408-07) to a final concentration of 25 nM with Dhamafect-1 diluted at 1:500 for OC316, HMCB, and A2058 and at 1:1000 for OVCAR8. Thirty hours later, cells were trypsinized, washed with cold PBS, fixed in 70% ethanol:water, pelleted, and resuspended in a staining solution containing 0.1% Triton X-100, 200 µg/ml DNase-free RNase A (Invitrogen, #12091-021), and 20 µg/ml Propidium Iodide (Roche, #11348639001). DNA content data was acquired from 10,000 cells using a Fortessa flow cytometer at 488 nm. Cell cycle distribution analysis was performed with Flowjo software (www.flowjo.com).

In Silico Analysis

Analysis of patient data was made possible by The Cancer Genome Atlas (TCGA) project. The results included are in part based upon data generated by the TCGA Research Network: http://cancergenome.nih.gov/ (Cancer Genome Atlas Research, N., et al., 2013). TCGA Level_3 RNASeq V2 Illumina HiSeq data was downloaded via the TCGA bulk download site (https://tcga-data.nci.nih.gov/tcga/). TCGA gene-level RSEM values (RNAseq by Expectation-Maximization) (Li, et al., 2011) were collated with patient annotation details using python v3.4. Tumor-matched normal tissue sample data was collected where available but was available only for a subset of tumor types. Therefore, to facilitate comparison of non-tumor samples from a broad range of tissues, data was also collected from the GTEx Consortium (Consortium, 2015). GTEx gene-level RPKM values (from a Novartis data repository) were collated and summarized using python v3.4. Violin plots of expression distributions were generated in R v3.2.0 using the ggplot2 package. Determination of sample outliers for UBC:UBB ratio (calculated in Spotfire v6.5) was defined as 1.25, based on the upper inner fence of the ratio, a standard statistical measure of outlier status, defined as Q3+1.5*IQ). Kernal density estimates were calculated in R v3.2.0 using the mclust package (Fraley, et al., 2012), where Bayesian information criterion (BIC) supports the presence of two Gaussian components for UBB expression in ovarian tumors with singular population estimates for the other ubiquitin genes (data not shown). Kaplan-Meier survival estimates were generated in R v3.2.0 using the survival package (Therneau TaL, 2015), with ovarian tumors stratified by the first quartile of UBB expression (low=$\log_2$(UBB)<Q1, high=$\log_2$(UBB)>Q1). Cancer cell line encyclopedia levels of expression and copy number of the ubiquitin genes UBB, UBC, UBA52, and RPS27A as well as the control GAPDH were derived from GC-RMA normalized Affymetrix Human Genome U133 Plus 2.0 microarray measurements available at www.broadinstitute.org/ccle (Barretina, et al., 2012).

shRNA Cloning and Viral Packaging shUBC821 (target sequence 5' CGAGAACGT-CAAAGCAAAGAT (SEQ ID NO:1)), shPLK1 (AT-CACAGAATCGTCGTATGCA (SEQ ID NO:2)), shLUC (CGATACTACCTACGGCAAATT (SEQ ID NO:3)), shNT (TGGTTTACATGTCGACTAA (SEQ ID NO:4)) forward and reverse complementary oligonucleotides were purchased from IDT, annealed following denaturing at 95° C. for 2 minutes, and then allowed to cool to room temperature in annealing buffer (10 mM Tris 8.0, 50 mM NaCl, 1 mM EDTA). These annealed oligonucleotides were ligated into the doxycycline (Dox)-inducible plasmid pRSI16 at a unique BbsI site (Cellecta). Newly constructed plasmids were confirmed by sequencing with the "U6S" primer (CAAGGCTGTTAGAGAGATAATTGGA (SEQ ID NO:5)). Packaging of vector into viral particles was done as follows. Briefly, shRNA plasmid vector was co-transfected into 293T cells along with the packaging and envelope vectors A8.9 and VSV-G at a 6:6:1 molar ratio using Lipofectamine 2000 (1:500 dilution). Supernatant was collected 48 hours later, and viral titer was determined by following infection in the presence of 5 µg/ml polybrene. After 24 hours, media was changed and viability was assessed in replica cultures grown for 7 days in the absence or presence of 1 µg/ml puromycin (puro).

Rescue of UBC Knockdown Toxicity by Expression of UBB

UBB cDNA cloned into pDEST40 was purchased from Invitrogen (IOH56688), and its sequence was validated by primer walking. pDEST40 empty vector (pVec) or pDEST40:UBB (pUBB) was transfected into OVCAR8 cells harboring shUBC821 using Lipofectamine LTX with PLUS Reagent_(Invitrogen, #15338030). Twenty four hours later, G418 (200 µg/ml, Gibco, #11811-023) was added for 7 days. G418-resistant cells were maintained in RPMI supplemented with 10% tetracycline-free FCS, puro (1 µg/ml) and G418 (200 µg/ml). Cells were seeded into four 6-well plates (200,000 cells/well) with media containing or lacking 100 ng/ml Dox to induce shRNA expression, and colony formation was performed as described. To detect UBB transcripts under the control of the CMV promoter in the pDEST40 vector, a CMV-UBB probe set was designed to the junction portion of the CMV promoter and UBB cDNA using IDT PrimerQuest Real-Time PCR Design tool and included the forward primer GACC-CAAGCTGGCTAGTTAAG UBB (SEQ ID NO:6), reverse primer CCTCAAGGGTGATGGTCTTG (SEQ ID NO:7), and probe FAM/AGGCACCATGCAGATCTTCGTGAA/TAMSp (SEQ ID NO:8). To measure expression of UBB coming from the plasmid, RNA was isolated 24, 48 and 72 hours after addition of Dox.

Western Blotting

HMCB (shUBC821 or shNT or shPLK1) and A2058 (shUBC821) cells were plated into 6-well plates (1,000,000 cells/well), and Dox (100 ng/ml) was added the next day. Cells were harvested at 12-hour intervals after addition of Dox in RIPA buffer (Teknova, #R3792) supplemented with Halt protease inhibitor cocktail (Thermo Scientific, #1861278) and Halt phosphatase inhibitor (Thermo Scientific, #1861277). The following antibodies were used for protein biomarker detection: ubiquitin (#3933), c-Myc (#5605), Phospho-H2A.X-S139 (#2577), caspase9 (#9502), BiP/Grp78 (#3183), α-tubulin (#3873), histone H2A.X (#7631) [from Cell Signaling Technology], and Caspase (#AB3612) [from Millipore]. Secondary antibodies were purchased from Odyssey (#926-32211, 926-68020), and fluorescence was detected using an Odyssey LI-COR.

Analysis of protein lysates following Dox time course was performed a minimum of 2 times.

Mouse Study

For animal studies, sample sizes were chosen according to our previous experience with similar study design and animal models in agreement with this type of work reported in the literature. OVCAR8 cells harboring shRNAs were luciferized by infecting with pMMP-LucNeo retrovirus (Sheng, et al., 2010) and selected with 100 ng/ml G418. Single clones exhibiting the highest Bright-Glo signal were selected for intraperitoneal implantation. All animal studies were performed according to protocols approved by the Dana-Farber Cancer Institute Institutional Animal Care and Use Committee. The experimental xenograft model was established by intraperitoneal injection of $2\times10^6$ OVCAR8.shControl or OVCAR8.shUBC cells in 6 week-old female NSG mice (Jackson Laboratory). Tumor growth was monitored weekly using the IVIS Spectrum In Vivo Imaging System (PerkinElmer), starting at day 9 post-cell injection. Briefly, mice were injected subcutaneously with 75 mg/kg D-luciferin potassium salt (Promega, E1605) in sterile PBS and anesthetized with 2% isoflurane in medical air. Serial bioluminescence images were acquired using the automated exposure set-up. The peak bioluminescence signal intensity within selected regions of interest (ROI) was quantified using the Living Image Software (PerkinElmer) and expressed as photon flux ($p/sec/cm^2/sr$). Representative planar bioluminescence images were displayed with indicated adjusted minimal and maximal thresholds. Mice were randomized into two groups per cell line, for a total of 4 groups (n=12 per group, 10 for efficacy and 2 for pharmacodynamics), using the overall tumor burden as measured by BLI. The recruited animals were randomized into treatment groups with similar BLI signal means, indicative of comparable disease burden. The investigators were not blinded to allocation during experiments and outcome assessment. Mean BLI for each group of 10 animals was calculated, and error was determined by SEM. Median survivals were determined using the method of Kaplan and Meier. A log-rank (Mantel-Cox) test was used to calculate P values derived from statistical analysis of the Kaplan-Meier survival curves. P values less than 0.05 were considered to be statistically significant. Analysis was performed with Graphpad Prism 6 (Graphpad software, Inc.). Standard chow was replaced with doxycycline chow (2,000 ppm) for one group in each cell line at day 37 post-cell injections and continued until study completion. All animals were further followed for survival. When signs of morbidity occurred (such as weight loss, jaundice, and/or ascites-associated bloating of the abdomen), the affected animal was euthanized according to the 2013 AVMA (American Veterinary Medical Association) guidelines. The animals were imaged weekly to assess tumor establishment and progression. As tumor burdens were comparable at 5 weeks post-cell injection, all animals were enrolled in treatment groups. A small number of animals developed palpable subcutaneous tumor, and were thus excluded from the study. As a result final efficacy study included 7-10 animals per group. On some occasions, the tumor lesions were excised, confirmed by ex vivo bioluminescence imaging, and stored in RNAlater (Ambion, AM7020) for further analysis. Tissue was homogenized in Trizol solution (Ambion, #15596-018), and RNA was isolated using the RNeasy Kit (Qiagen, #74106).

Resistance Studies tetR mRNA expression level was detected with a custom qPCR probe set (forward primer GCCTACAGAGAAGCAGTATGAG (SEQ ID NO:9), reverse primer AGAGGGCATACAAGGCATTT (SEQ ID NO:10), and probe FAM/AAGCCTTGTTGGCACAGGAATGC/TAMSp (SEQ ID NO: 11)). Measurement of hairpin expression was done using a custom probe designed and synthesized by Exiqon based on the shUBC target sequence CGAGAACGTCAAAGCAAAGAT (SEQ ID NO: 1). Total miRNA was made from parental and relapsed tumor cell lines with the miRNeasy Mini Kit (Qiagen, #217004). cDNAs were synthesized using miRCURY LNA Universal RT microRNA PCR Starter Kit (Exiqon, #203351) according to the manufacturer's recommendations. Briefly, a poly-A tail added to the mature shRNA transcript was used as an anchor for a poly-T primer to convert this into cDNA which was amplified using template-specific and LNA-enhanced forward and reverse primers, and product was detected by SYBR Green fluorescence and quantitated by protocol provided by Applied Biosystems 7900 realtime PCR. The parental cell line OVCAR8(shUBC821) and Dox-resistant xenograft derivatives were cultured in RPMI containing 10% tet-free FCS and 1 µg/ml puro. Cells were transfected with siRNAs at a final concentration of 5 nM, as described. CTG was measured 72 hours later, and UBC mRNA was measured 24 hours after transfection. Six days after transfection, cells were fixed and stained with crystal violet, as described.

Example 1. UBB Silencing in Human Gynecological Cancer

We examined the expression data from TCGA samples across 27 tumor types (www.cancergenome.nih.gov) and found that expression of the polyubiquitin gene UBB is significantly decreased in a subset of patients from the ovarian (OV) dataset (FIG. 1a). RNASeq data is shown for each patient, represented as a dot, and compares expression of each of the four ubiquitin-encoding genes along with GAPDH as an internal control for sample quality and distribution normalcy. We find that the other three ubiquitin-encoding genes are expressed in tight, unimodal distributions, as is GAPDH (FIG. 1a). We also note the variant distribution of UBB RNA across ovarian patients is not seen in samples from lung or thyroid cancer patients nor in RNA from normal ovarian tissue (FIG. 1b).

Figure 7:
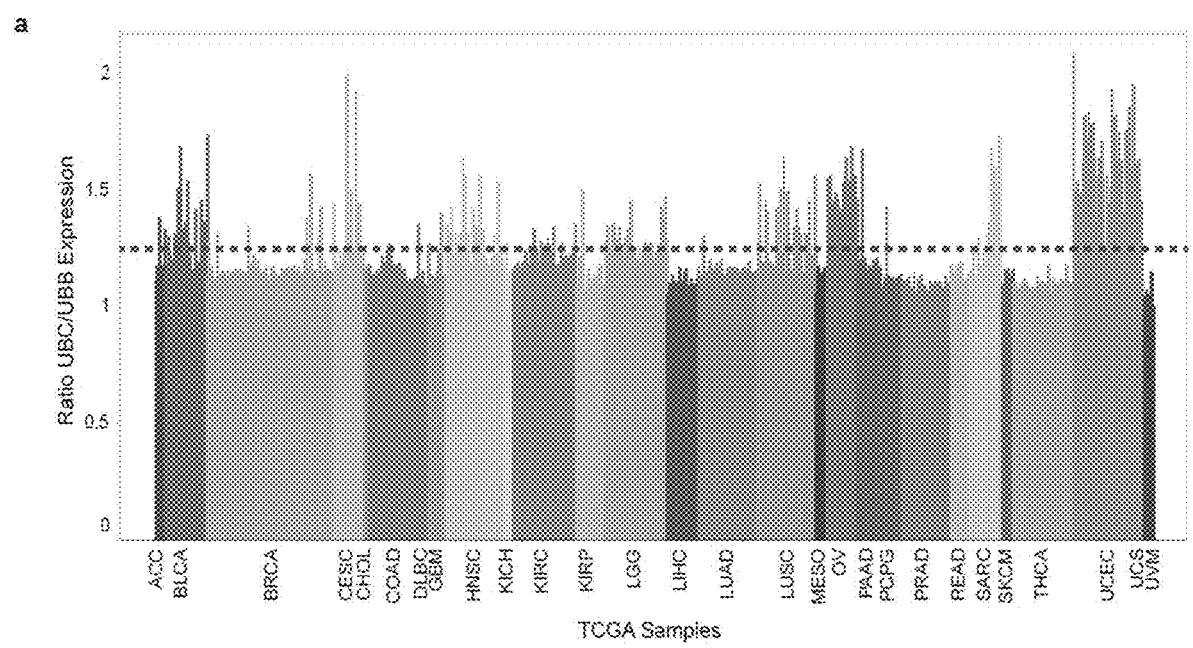
FIG. 7. Expression levels of UBB within each patient-derived tumor across TCGA is shown as the ratio of UBC:UBB. Dashed line shows upper inner fence cutoff and distinguishes outlier patients for low UBB expression.

The two human polyubiquitin genes, UBB and UBC, are typically expressed at roughly equivalent levels in cell lines, in normal tissues as well as in tumor samples. We therefore used the ratio of UBC to UBB mRNA to identify relative expression outliers across TCGA samples while normalizing sample variability. Determining the outliers in the 10% high or low expression range extremes (see statistic in FIG. 1c) reveals a high frequency of low UBB outliers in tumors of the female reproductive tract, ranging from just over 16% in uterine sarcoma to almost 30% in ovarian cancer (FIG. 1c). Low UBB expression outliers can be seen in many other tumors shown as box plots although the frequency of UBB down-regulation is substantially lower that that seen in gynecological tumors (FIG. 1c, bottom). Another view of these data shows ratios on a patient-by-patient basis (FIG. 7). Looking at expression in normal tissue we do not see a similar population of low UBB expressing outliers (FIG. 1b), suggesting that UBB repression is tissue-type specific and recurrent in gynecological cancers.

To understand the impact that UBB silencing may have on clinical outcomes, we considered the long-term survival of patients in the lowest quartile of UBB expression compared with the remainder (FIG. 1d, top). These patients have a poorer outcome in overall survival (FIG. 1d, bottom), indicating that UBB repression is associated with more aggressive disease and clinical significance of our observation.

Example 2. Silencing of UBB Establishes Dependence on UBC

As a basis for considering the functional implications of these observations, we wanted to know if we could identify cell lines expressing UBB at low levels, presumably derived from patients such as those described above. For this objective, we surveyed expression of ubiquitin-encoding genes across the entire CCLE, which consists of >1,000 cell lines from 24 tumor types (Barretina, et al., 2012) (FIG. 2a). UBB expression is strongly decreased in a subset of cell lines, while expression of the three other ubiquitin genes in these cells remains within a relatively tight distribution shared among all cells. This is also seen in box plots representing the same data (FIG. 2b), which clearly reveal a group of outliers with low levels of UBB expression. Importantly, identifying UBB silencing in relevant cell lines enables us to pursue functional studies to determine the translational value of this finding.

This analysis identified 26 cell lines in which UBB expression is strongly suppressed, with the highest number derived from endometrial, ovarian, and skin cancer patients, though other lineages are included (Table 1). These data indicate that UBB expression is regulated independently of other genes encoding ubiquitin and that UBB repression observed in tumors is likely to be maintained in cell lines derived from these patients. The highest frequency of UBB repression occurs in cell lines derived from ovarian and endometrial cancers, and almost 15% of cell lines derived from these lineages express very low levels of UBB (Table 2). This representation parallels our observations of UBB expression in the TCGA dataset and provides independent support that repression of UBB is primarily occurring in gynecological cancers.

TABLE 1

Cell lines with UBB in OFF state

| Cell Line | Lineage |
|---|---|
| nb1 | autonomic ganglia |
| ks1 | central nervous system |
| efe184 | endometrium |
| hec1a | endometrium |
| mfe280 | endometrium |
| ten | endometrium |
| em2 | CML |
| st486 | Burkitt's lymphoma |
| snu283 | large intestine |
| jhh1 | liver |
| ncih82 | Lung-small cell |
| ncih322 | Lung-adenocarcinoma |
| kyse150 | esophagus |
| caov4 | ovary |
| jhoc5 | ovary |
| jhom1 | ovary |
| ovk18 | ovary |
| ovcar8 | ovary |
| rmugs | ovary |
| snu8 | ovary |
| colo818 | skin |
| hmcb | skin |
| k029ax | skin |
| skut1 | leiomyosarcoma |
| cal33 | upper aerodigestive |
| yd38 | upper aerodigestive |

TABLE 2

Lineage frequency of $UBB^{OFF}$ in CCLE

| Lineage | $UBB^{off}$ | Total | Frequency |
|---|---|---|---|
| autonomic ganglia | 1 | 16 | 0.063 |
| biliary tract | 0 | 8 | na |
| bone | 0 | 26 | na |
| breast | 0 | 71 | na |
| central nervous system | 1 | 55 | 0.018 |
| endometrium | 4 | 28 | 0.143 |
| eye | 0 | 7 | na |
| haem and lymph | 2 | 191 | 0.011 |
| kidney | 0 | 23 | na |
| large_intestine | 1 | 68 | 0.015 |
| liver | 1 | 28 | 0.036 |
| lung | 3 | 185 | 0.016 |
| esophagus | 1 | 26 | 0.038 |
| ovary | 7 | 52 | 0.135 |
| pancreas | 0 | 47 | na |
| pleura | 0 | 14 | na |
| prostate | 0 | 7 | na |
| salivary gland | 0 | 2 | na |
| skin | 4 | 79 | 0.05 |
| soft tissue | 1 | 23 | 0.043 |
| stomach | 0 | 39 | na |
| thyroid | 0 | 12 | na |
| upper aerodigestive track | 2 | 33 | 0.061 |
| urinary track | 0 | 27 | na |

To study this in more detail, we selected a group of cell lines from different tumor types based on UBB expression levels. Initially we wanted to confirm UBB expression in these cell models and found that UBB expression levels are consistent with the CCLE profiling data (FIG. 2c). Importantly we observe potent UBB mRNA reductions in a subset of cell lines, referred to as $UBB^{LO}$ including CAL33 (tongue), HMCB (skin), JHOM1 (ovarian), KS-1 (brain), KYSE150 (endometrial), OVK18 (ovarian), and OVCAR8 (ovarian).

As polyubiquitin genes, UBB and UBC can contribute disproportionately to the pool of cellular ubiquitin protein on a per transcript basis relative to the UBA52 and RPS27A genes, which each encode a single ubiquitin polypeptide as a fusion protein with large and small ribosomal proteins, respectively. We wanted to consider whether cells repressed for UBB had an increased dependence on UBC to maintain their ubiquitin pool. To address this, we silenced UBC in cell lines with normal or reduced levels of UBB. siRNA-mediated knockdown of the essential gene PLK1 is a control for viability effects and additionally provides a basis for assessing transfection efficiency. All cell lines in this panel are dependent on PLK1. By contrast, knockdown of UBC produces a viability phenotype only in the cells with low UBB expression (FIG. 2d, red bars).

To consider this phenotype in more depth, a panel of lines comprising four $UBB^{LO}$ and six $UBB^{WT}$ lines were transfected with a dose titration of validated, gene-specific siRNAs while maintaining total siRNA concentration at 20 nM by using non-targeting siRNAs as filler. Titration of siRNAs that target UBC mRNA results in minimal viability effects in most $UBB^{WT}$ lines. The largest effect we observe for UBC knock-down in a $UBB^{WT}$ line, occurs in the ovarian line OC316, for which 5 nM of UBC siRNA produces a 50% drop in viability at 72 hours (FIG. 3a). By contrast, in the $UBB^{LO}$ lines included in our panel, UBC siRNAs produce a consistent drop in viability that ranges between 20 and 100-fold with 1 nM UBC siRNA (FIG. 3a). We note that at a concentration of 0.160 nM UBC siRNA, viability phenotypes in lines with reduced UBB expression is still greater than 10-fold below control transfected cells. These phenotypes are substantially more potent than those seen with PLK1 knockdown, which produces on average a ~5-fold decrease in viability at 1 nM siRNA. Measurement of UBC mRNA in siRNA titration studies found that knockdown was relatively stable between 60-80% across the siRNA dilution range used (FIG. 8a).

Given previous reports of compensation among ubiquitin genes in UBC null cells we considered whether phenotypes due to UBC knockdown, while potent, were durable or if there was some capacity, over time, to adapt to these shifts in ubiquitin pools (Ryu, et al., 2007). Colony formation was used to address this question following siRNA transfection. Our positive control for these studies was PLK1 siRNA, and, as observed in the short-term assay, PLK1 is also essential for long-term viability for all cells tested (FIG. 3b). UBC knockdown prevents colony formation selectively in cells with low levels of UBB expression cells consistent with the short-term viability experiments. Growth of these cells was continuously monitored following siRNA transfection with real-time, live-cell imaging and we found that depletion of UBC from cells with normal levels of UBB, OC316 and A2058, results in a modest, short-term reduction in growth rate and achieve confluence one day later than for cells treated with control siRNA (FIG. 8b,c). By contrast, the UBB$^{LO}$ cells cannot compensate and loss of UBC leads to an irreversible loss of viability.

Figure 8:
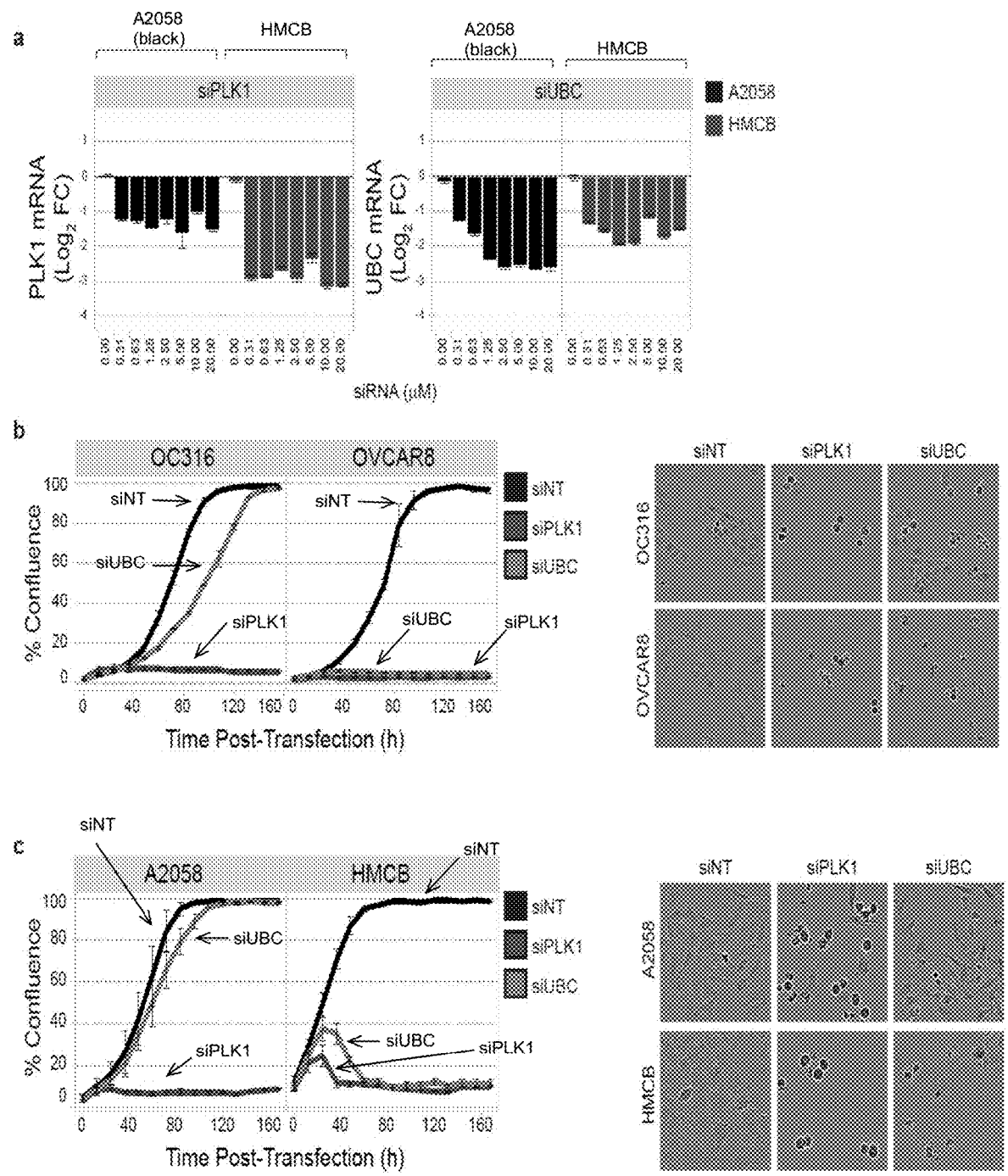
FIG. 8. siRNA titration and cell viability by live cell imaging. (a) Dose titration of siRNA for PLK1 and UBC in OC316 (black) and OVCAR8 (red) cells leads to knockdown of target mRNA. For all samples, the concentration of target siRNA is shown on the X-axis; however, in each transfection, the total siRNA amount was adjusted to 20 nM with non-targeting control siRNA. This experiment was performed in ovarian (OC316, OVCAR8) and skin (A2058 and HMCB) cancer cell lines, with one line from each lineage having a transcriptionally silent UBB locus (OVCAR8, HMCB). (b,c) Growth of cells was monitored using Incucyte (Essen) real-time microscropy to monitor growth of cells. siRNAs targeting PLK1 were lethal to all four cell lines, whereas knockdown of UBC was lethal only in the UBB$^{LO}$ lines, OVCAR8 and HMCB. (Right) Phase contrast images of cells 36 hours post-transfection. The study with the ovarian lines was repeated six times, and the study with the melanoma lines was repeated twice.

To consider the impact of ubiquitin depletion on cell cycle progression, two pairs of cell lines matched by lineage (skin and ovarian) were used in subsequent transfection studies (FIG. 3c,d). Knockdown of UBC in both of the UBB$^{LO}$ lines results in an accumulation of cells in G2/M. This resembles the effects of PLK1 knockdown, previously described to block cells at cytokinesis (Liu, et al., 2002), which we similarly observed (FIG. 8).

Example 3. Synthetic Lethality Based on Polyubiquitin Genes

Figure 4:
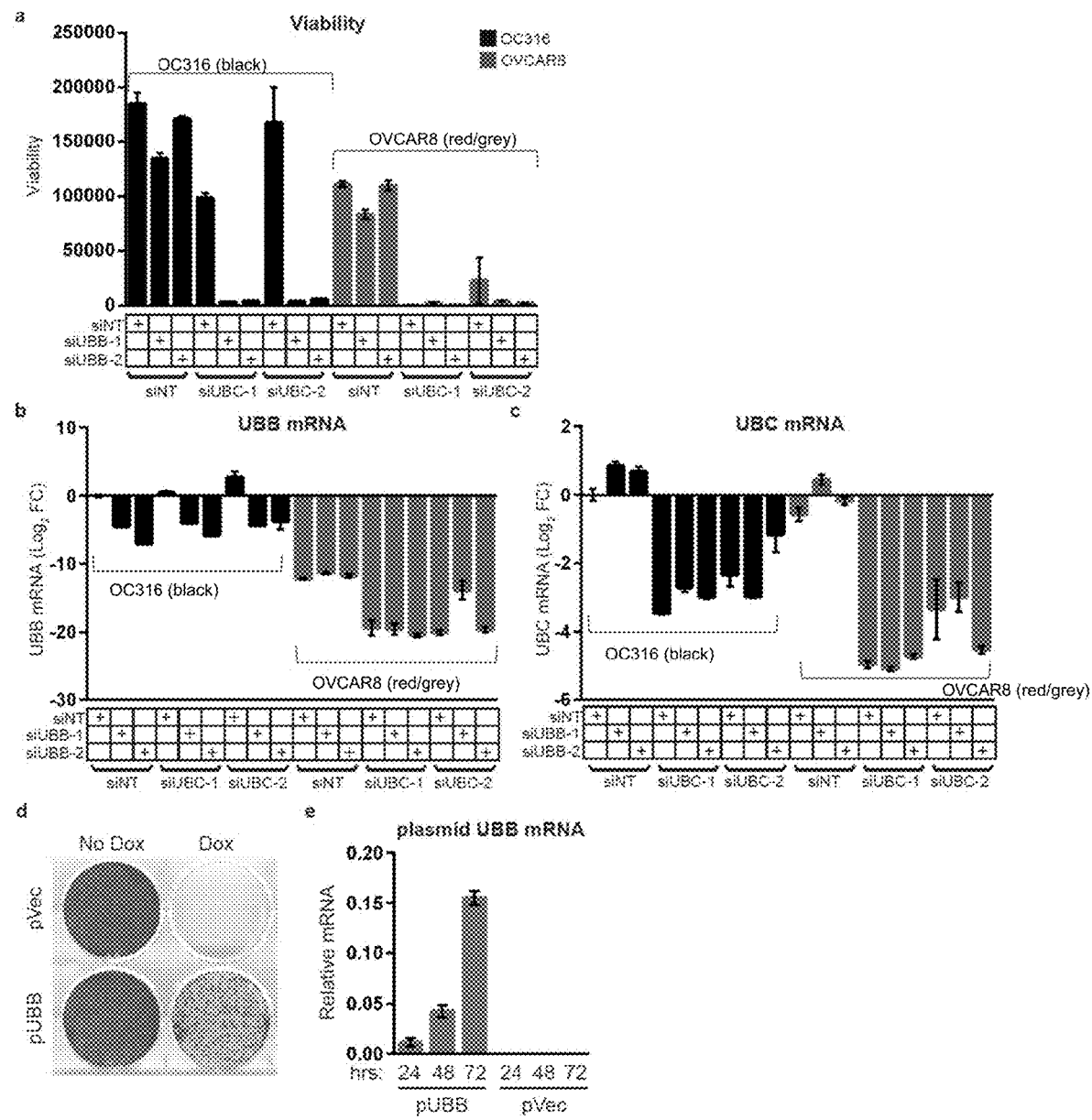
FIG. 4. UBB and UBC are a synthetic lethal gene pair. (a) OC316 (black) and OVCAR8 (red) cells were transfected as biological quadruplicates with a combination of two siRNAs at 5 nM each as shown in the matrix below the figure. siRNAs for UBC and UBB were combined with each other or with control NT siRNA and viability was determined 72 hours post-transfection. The study was performed twice in multiple cell line pairs (see FIG. 9). (b,c) mRNA levels of (b) UBB and (c) UBC as $\log_2$ fold-change relative to OC316 siNT control 24 hours post-transfection among biological quadruplicates. (d) Colony formation assays of OVCAR8-shUBC cells transfected with a plasmid encoding UBB-neo (pUBB) or the empty neo vector alone and G418-resistance cells were seeded into 6 well plates with or without Dox (100 ng/ml). 7 days later cells were fixed and stained with crystal violet. (e) Expression from pUBB is measured on three successive days after addition of Dox.
Figure 9:
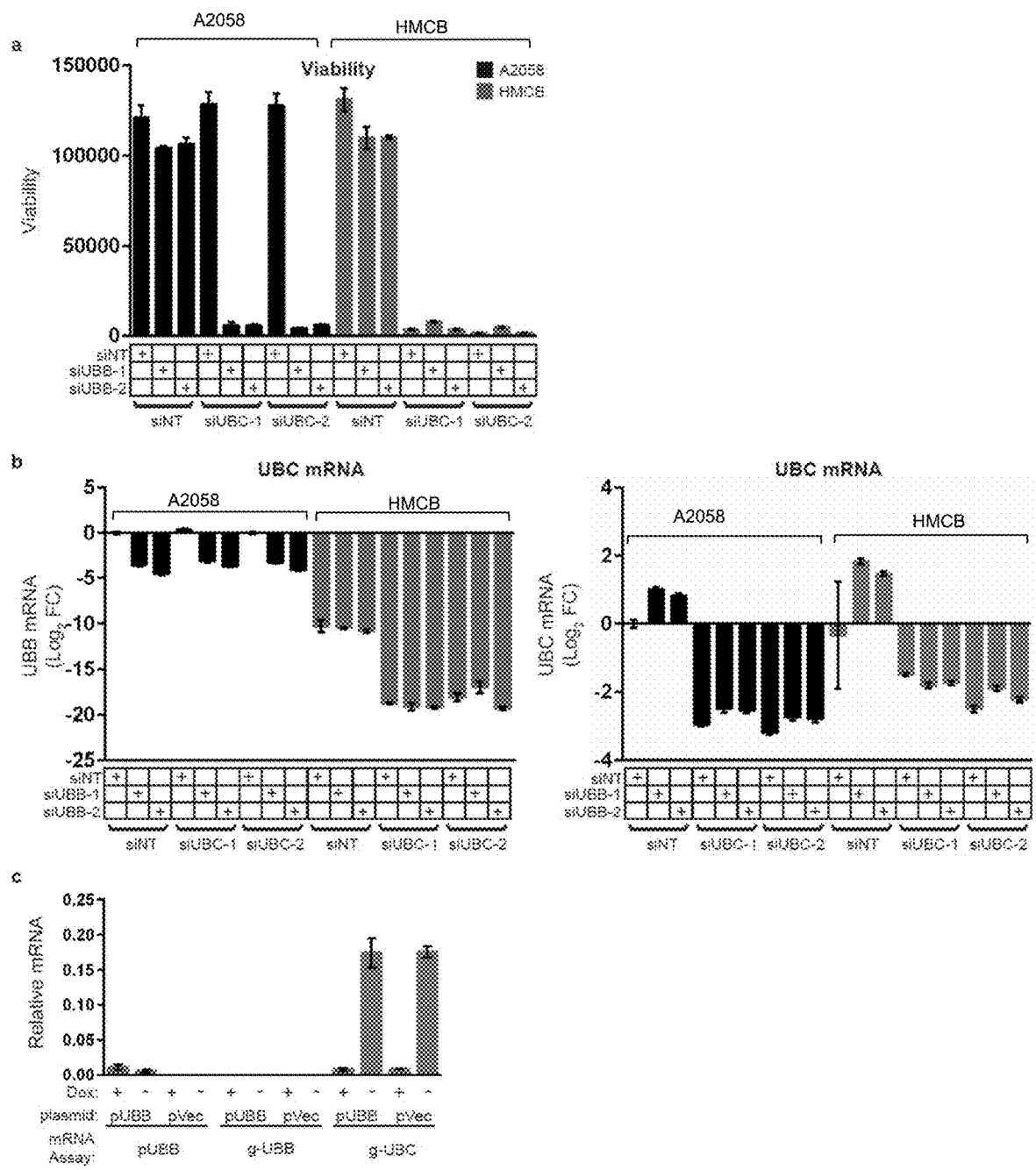
FIG. 9. UBB and UBC are a synthetic lethal gene pair. (a) Skin cancer cell lines A2058 (black) and HMCB (red) cells were transfected with a combination of two siRNAs shown in the matrix along the X-axis. Every pairwise combination of 2 siRNAs for UBC, UBB and NT were used to transfect these cells, and viability was measured 72 hours later. A2058 are viable after transfection combining (siNT+siUBC), whereas HMCB are sensitive to that combination. Both lines are sensitive to the combination containing (siUBB+siUBC). (b) siRNA-mediated knockdown of mRNA for UBB (top) and UBC (bottom) are shown as fold-change ($\log_2$) relative to siNT for A2058 controls 24 hours after transfection. (c) Expression of the plasmid-borne UBB (pUBB), endogenous, genomic, UBB (gUBB) and UBC (gUBC) in transfections into OVCAR8 cells harboring Dox-inducible shUBC lentivirus described in FIG. 4d. RNA was isolated 24 hours post-transfection. While gUBB mRNA is undetectable, pUBB is expressed at low levels and gUBC mRNA shows strong Dox-dependent knock-down.

Our data suggest that the reduced level of UBB expression establishes the dependence on UBC. However, our studies have focused on cells that may have adapted to low levels of UBB over time, so we wanted to test whether knocking down UBB de novo would be sufficient to establish a dependence on UBC. In UBB$^{WT}$ OC316 (ovarian) cells, knockdown of either UBC or UBB individually is tolerated; however, silencing of these genes in combination results in synthetic lethality (FIG. 4a-c). These results are similar to those obtained upon knockdown of UBC singly in UBB$^{LO}$ OVCAR8 cells. The same results were obtained with a UBB$^{WT}$ and UBB$^{LO}$ pair of melanoma lines (FIG. 9).

We also find that the dependency on UBC in OVCAR8 cells can be suppressed by re-expressing UBB. For this experiment, we used OVCAR8 (UBB$^{LO}$) cells containing a doxycycline (Dox)-inducible UBC shRNA. In the presence of Dox, these cells are efficiently eliminated (FIG. 4d). However, expressing UBB from a plasmid (pUBB) rescues Dox-induced lethality mediated by silencing of UBC (FIG. 4d,e). These results establish that the primary determinant of lethality to UBC knockdown is a low level of UBB expression.

Example 4. Cellular Response to a Ubiquitin Catastrophe

Figure 5:
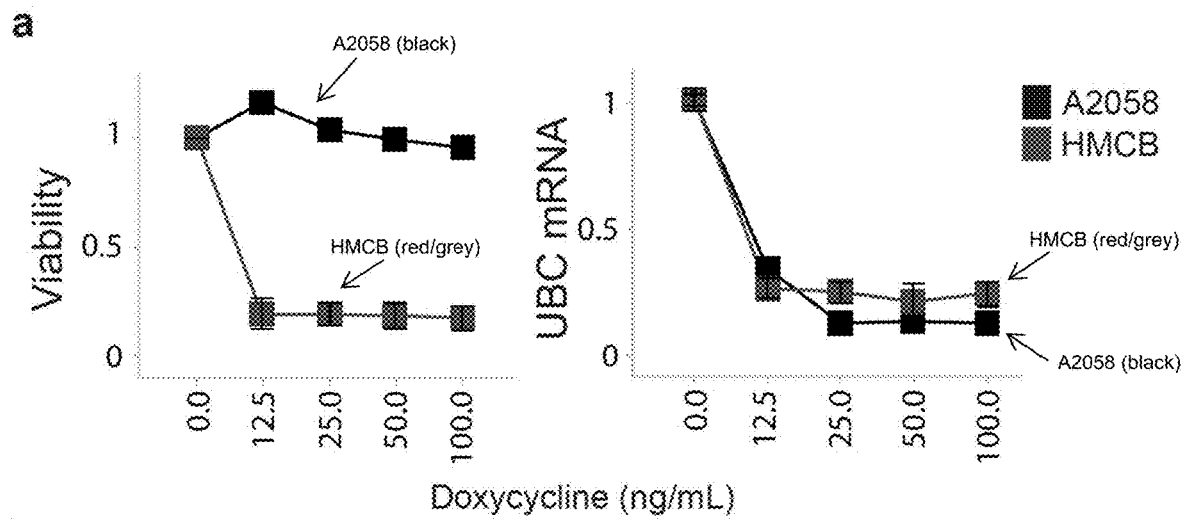
FIG. 5. Knockdown of UBC in UBB$^{LO}$ cells causes loss of viability and induction of biomarkers of a ubiquitin depletion catastrophe. (a) Viability effects at 72 hours (left) in UBB$^{WT}$ (A2058, black) or UBB$^{LO}$ (HMCB, red) melanoma cells transduced with a Dox-inducible shUBC hairpin and exposed to a dose titration of Dox. Knockdown of UBC mRNA is shown at right (at 48 hrs post-Dox). (b) HMCB cells with shUBC or control shNT were treated with 100 ng/ml Dox, and protein lysates were prepared at time of Dox addition and at 12, 24, 36, and 48 hours thereafter.

Using an inducible shRNA system enables a regulated, pan-cellular, and stable approach to study this ubiquitin-mediated synthetic lethal process. Cells transduced with the UBC shRNA vector were treated with a dose titration of Dox (FIG. 5a, left). Dox produces a viability phenotype in HMCB (UBB$^{LO}$) cells with little effect in A2058 (UBB$^{WT}$) cells. Knockdown of UBC mRNA is near maximal for both lines at doses greater than 12.5 ng/ml (FIG. 5a, right).

The ubiquitin proteins produced from each of the four ubiquitin-encoding loci is identical. While we cannot differentiate ubiquitin protein coming from the UBB or UBC locus, we could assess global protein ubiquitination as a reflection of cellular ubiquitin pools. HMCB cells harboring an inducible shUBC were treated with Dox, and lysates were prepared at 12-hour intervals (FIG. 5b). The level of protein-ubiquitin conjugates remains stable for the first 12 hours after addition of Dox but drops precipitously during the next 12-hour period and continues to drop over the remainder of the time-course.

The depletion of ubiquitin and ubiquitinated proteins is specific to UBC knockdown in the UBB$^{LO}$ cells and is not seen in UBB$^{WT}$ A2058 cells (FIG. 10b). Unexpectedly, the levels of BiP (also known as Grp78 or HSPA5), the ER sensor of unfolded or damaged proteins, remain unaffected (FIG. 5b), suggesting that ER stress is not induced and not likely to be the cause of the viability phenotype. In the same samples, we observe increases in c-MYC protein, cleaved forms of caspase 9, and γ-H2AX, (FIG. 5b) suggesting that further loss of ubiquitin in UBB$^{LO}$ cells may phenocopy proteasome inhibition, stabilizing short-lived proteins and leading to initiation of apoptosis.

Example 5. In Vivo Confirmation of Synthetic Lethality

Figure 6:
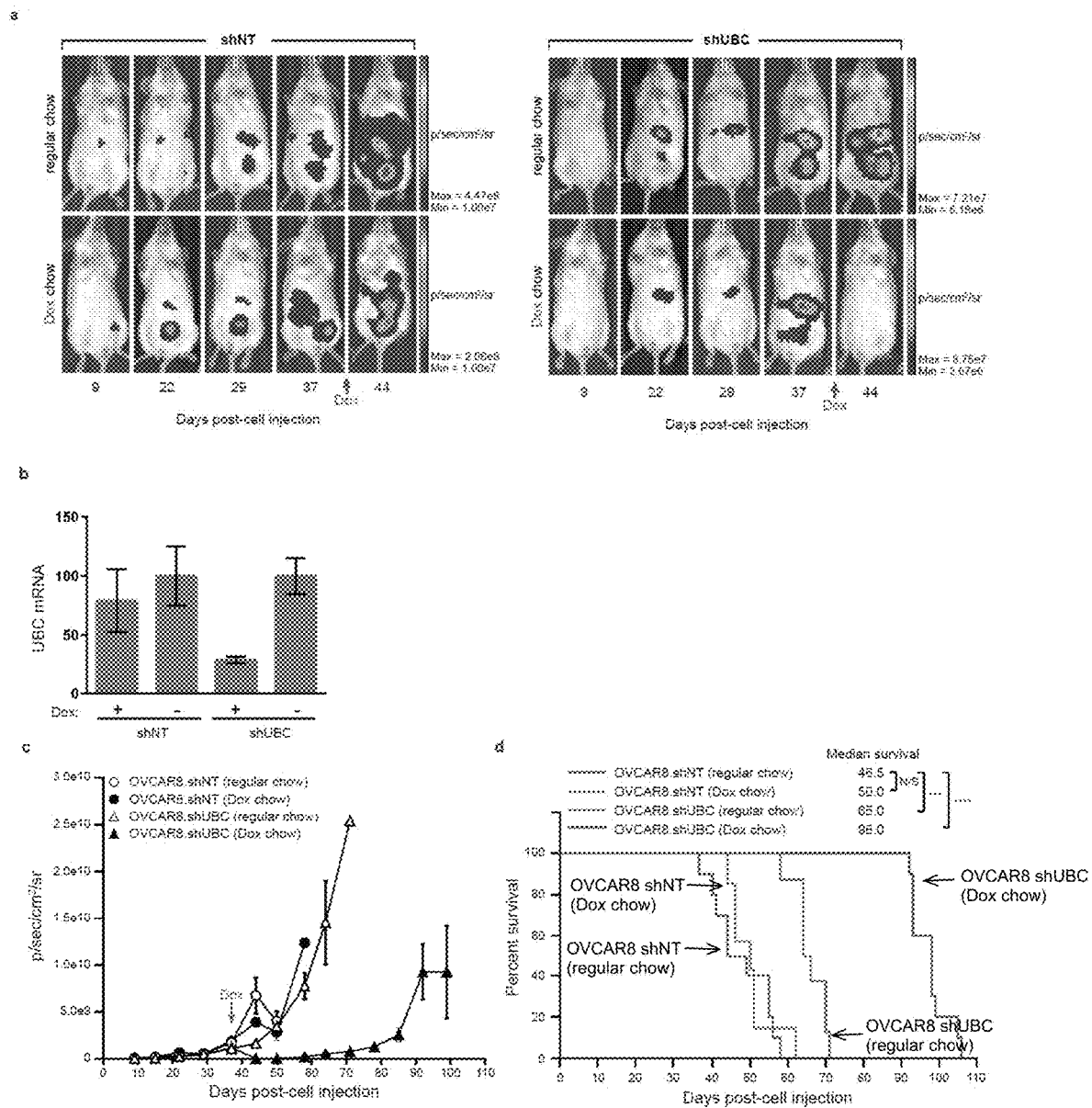
FIG. 6. In vivo validation of UBB/UBC synthetic lethality. (a) Xenogen images are shown for mice on days 9, 22, 29, 37, and 44 post-implantation with luciferized OVCAR8 cells. Cells were previously transduced with Dox-inducible shNT (top two rows) or shUBC (bottom two rows). On day 37 post-implantation, half of the mice were transitioned to Dox-containing chow. (b) Pharmacodynamic study of UBC mRNA knockdown 36 hours after the shift to Dox chow. RNA was prepared from multiple tumor nodules from two mice per group, and UBC levels were normalized to NT control (No Dox). Error is calculated by standard deviation. (c) Total averaged bioluminescence for 10 mice per arm. Samples derived from shNT with Dox (closed circles) or without Dox (open circles) and shUBC mice with Dox (closed triangles) or without Dox (open triangles). Standard error of the mean (SEM) is shown. (d) Kaplan-Meier plot shows the percentage of mice surviving in each arm of study. All mice in the shNT arm succumb by day 60, and addition of Dox does not affect viability for shNT. Mice bearing tumors with shUBC (blue, red) have increased survival. For the mice receiving no Dox (blue), this extension of survival may be owing to slight leakiness of the shUBC hairpin. Statistical significance indicated by p values as follows: not significant (N/S)=0.61; *=p<0.0002; **=p<0.0001. Variation among the groups is substantially less than the difference between the shUBC+Dox and other groups.

These observations encouraged us to consider whether repression of UBB represents a therapeutically exploitable vulnerability in a more physiologically relevant context. For this study, luciferized OVCAR8 cells transduced with a Dox-inducible shUBC vector or a non-targeting shRNA were implanted orthotopically into 24 NSG mice. Tumor-bearing animals were randomly assigned to one of two study arms: 12 would receive Dox by chow and 12 would continue to receive normal chow. On day 37, Dox treatment was initiated at a time when all animals had established tumor burdens readily documented by luciferase-dependent imaging. Within 5 days of starting Dox chow diet, bioluminescent (BLI) values had dropped below detection levels in mice bearing the shUBC transduced tumor cells (FIG. 6a). During the same period BLI values which were monitored bi-weekly had increased for all other mice (FIG. 6a). We observed a shUBC-specific decrease in UBC mRNA in these tumors (FIG. 6b), and conclude that the dependency on UBC in the UBB$^{LO}$ cells is also relevant in an in vivo setting.

We further used this model to determine the survival benefit of targeting UBC in these cells. Animals in the control arms developed symptoms of liver failure due to tumor cell growth and rapidly succumbed to disease with median survival around 50 days (FIG. 6d). By contrast, mice implanted with OVCAR8.shUBC and continuously fed Dox chow had durable remissions and substantial long-term survival benefit. However, these tumors did develop resistance (FIG. 6c), and the mice eventually died with a median survival of nearly 100 days post-implant.

Figure 10:
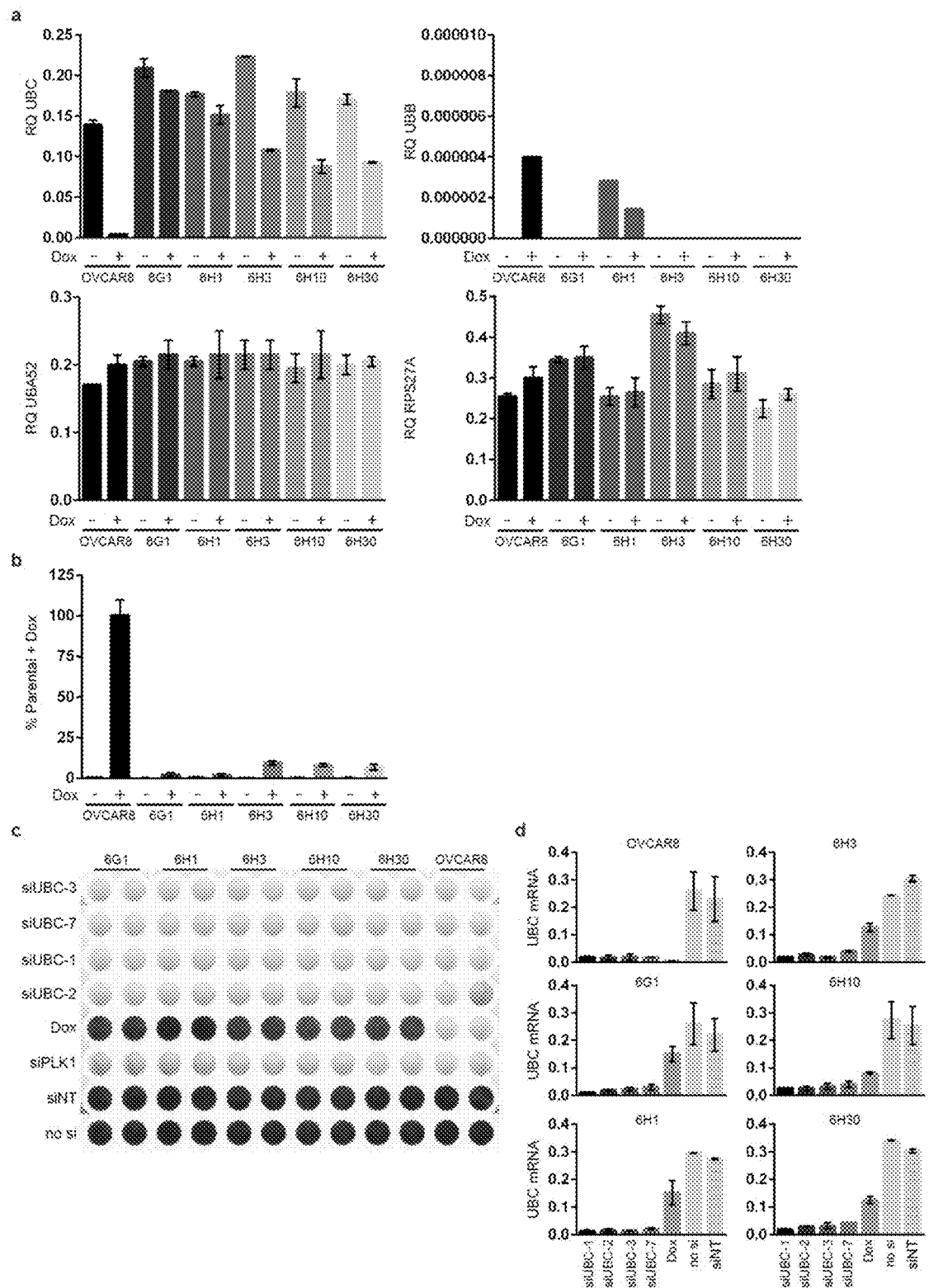
FIG. 10. Dox-resistant tumor cells grown ex vivo remain sensitive to UBC knockdown by siRNA. (a) Expression levels of each of the ubiquitin genes in parental OVCAR8 and in tumor tissue from five mice that developed resistance to Dox treatment in vivo (6G1, 6H1, 6H3, 6H10, 6H30) are shown. In the parental OVCAR8-shUBC cells Dox treatment produces a marked reduction of UBC mRNA (upper left, labeled OVCAR8) which is attenuated to various extents in each of the resistant lines. Expression of monoubiquitin genes UBA52 (lower left) and RPS27A (lower right) are unaffected by Dox treatment. Levels of UBB (upper right) mRNA is at the limits of sensitivity. The very low levels of UBB expression in clone 6H1 is still below that seen in the parental cells. Note that the Y-axis is different for each gene due to varying levels of expression. (b) Levels of shUBC RNA which is strongly induced by Dox treatment in parental cells, is blunted in each of the Dox-resistant clones. Short RNAs were isolated, and qPCR was performed to assess levels of the UBC-targeting shRNA. (c) Colony formation following transfection of siRNAs that target UBC, PLK1, or NT in parental OVCAR8-shUBC cells and in the five Dox-resistant lines indicates that the latter retain sensitivity to UBC knockdown. Resistance to Dox (100 ng/ml) is retained in these ex vivo cultures, while parental OVCAR8-shUBC remain Dox-sensitive (far right columns). (d) UBC expression in each of the ex vivo established lines following transfection of siRNAs targeting UBC, PLK1, or NT control. The effect of Dox treatment on UBC levels in the ex vivo cell lines is shown compared to parental OVCAR8 (top left). Error is shown as standard deviation between biological replicates.

The resistant tumors provided an opportunity to determine whether there are potential 'on-pathway' adaptions, such as de-repression of UBB, that rescue lethality due to acute ubiquitin deficiency. Dox-resistant tumors were removed and re-established for growth in cell culture. Subsequent analysis revealed that endogenous UBC mRNA was no longer being knocked-down and we found that expression of the short hairpin for UBC had been silenced. All resistant lines still retained sensitivity to UBC siRNAs by transfection (FIG. 10). We conclude that while expression of ectopic UBB can rescue lethality caused by UBC knockdown (FIG. 4e), we did not observe re-expression of endogenous UBB as a mechanism of resistance in the in vivo model. Rather, we found that it was a loss of expression of the shRNA in response to Dox that

DISCUSSION

Our analysis of TCGA identifies transcriptional repression of UBB as a frequent alteration in gynecological cancers linked to poor survival, and we establish a therapeutic model yielding deep remissions in vivo based on this observation.

Why would UBB repression be selected for in cancer? Two recent studies in yeast might provide hints. First, experimental evolution of yeast growing on an alternative carbon source selected for loss-of-function mutations in UBR1, an E3 ubiquitin ligase involved in N-end rule degradation. In a second study the fitness of cells with detrimental mutations was restored by loss of genes in the ubiquitin pathway. Genes identified in these screens are involved in growth suppression networks and provides a basis for considering that UBB loss constitutes a fitness advantage in this lineage. Perhaps related, a genomics approach termed CYCLOPS that seeks to identify vulnerabilities arising from copy number loss, identified PSMC2, a component of the proteasome, as a recurrent event in a subset of ovarian cancers, which demonstrate increased sensitivity to PSMC2 knockdown (Nijhawan, et al., 2012). Hemizygous PSMC2 copy number loss and transcriptional repression of UBB might serve to optimize cell fitness by tuning protein fate in a way that stabilizes pro-survival proteins during tumorigenesis (Solimini, et al., 2012).

However, the loss of UBB leads to reductions in the ubiquitin pool, the benefit of which may ultimately be offset by the cost associated with shifting the cell closer to a minimal ubiquitin threshold. Such a threshold seems to be crossed selectively in $UBB^{LO}$ cells following UBC knockdown. This leads to a sharp decline in ubiquitin-conjugated proteins but does not activate the ER stress sensor BiP, which accompanies disruption of either proteasome activity or the ubiquitin-dependent ER associated protein degradation (ERAD) machinery (Claessen, et al., 2012).

The role of ubiquitin during the DNA damage response is well described (Al-Hakim, et al., 2010; Moldovan, et al., 2009). Induction of γ-H2AX in the context of acute ubiquitin depletion is consistent with previous observations that UBB and UBC suppress spontaneous DNA damage during otherwise unperturbed growth (Paulsen, et al., 2009) and are required for normal 53BP1 foci formation following irradiation (Stewart, 2009; Stewart, et al., 2009). Reductions in UBB expression might be expected to desensitize cells to the growth effects of DNA damage or to interfere with normal DNA repair.

In mammals, the polyubiquitin genes UBB and UBC play different roles in development. UBC-null mice die in mid-gestation due to disruption of fetal liver function (Ryu, et al., 2007; Park, et al., 2013; Ryu, et al., 2012), while mice that are homozygous null for UBB are viable but sterile (Sinnar, et al., 2011). According to TCGA data across all tumor lineages, silencing of UBB is primarily restricted to tumors of the female reproductive tract and may be related to an essential role of polyubiquitin genes for meiosis in yeast, fly, and mammals. UBB is expressed toward the lower end of the spectrum in normal adult female reproductive tissue, and this expression pattern may predispose cells to further reductions seen in tumors.

Figure 11:
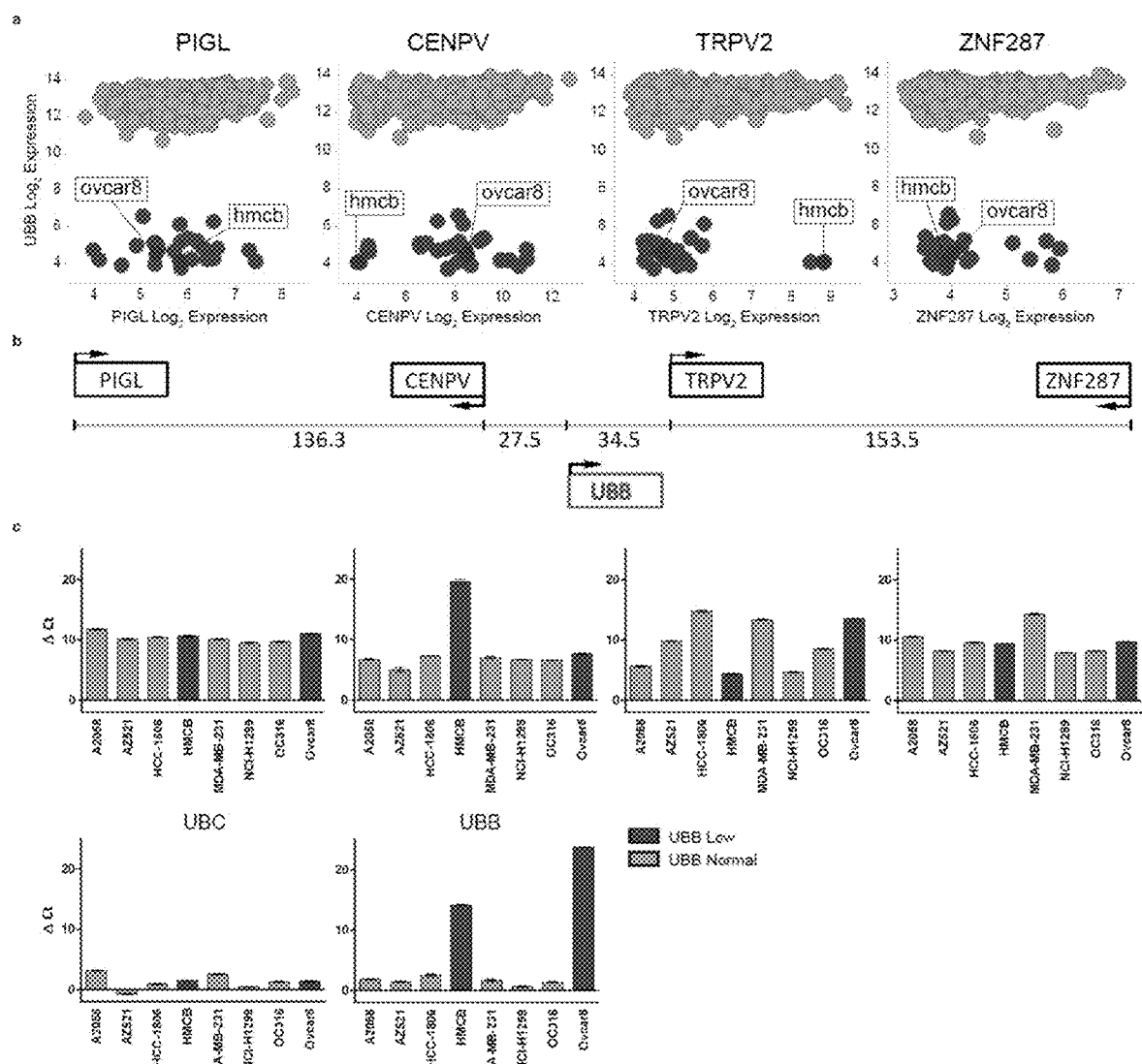
FIG. 11. Transcriptional silencing of UBB is regulated locally at a gene-proximal level. (a) Expression of the four nearest-neighbor genes to UBB shows that their transcription regulation is independent of UBB expression status across the CCLE. Each chart shows expression of four UBB nearest-neighbor genes, with UBB expression levels on the Y-axis and expression of each of the four genes along the X-axis. The $UBB^{LO}$ cell lines (red) OVCAR8 and HMCB are highlighted to illustrate divergent expression patterns of CENPV and TRPV2 in these cells. (b) Linear map of UBB region from chromosome 17p12 showing distances and orientation of transcription start sites in kilobases. (c) mRNA expression levels of four genes flanking UBB were measured in eight cell lines. Increasing ΔCt values indicates decreased expression and confirms CCLE profile database. Expression of UBC and UBB is shown in these cell lines at bottom. Technical quadruplicates were analyzed by qPCR.

Repression of UBB is unlikely to be a random event. It occurs specifically in gynecological cancer by a locally restricted mechanism that does not extend to the closest flanking genes, CENPV or TRPV2, which are located just 28 kb to the 5' and 35 kb to the 3' side, respectively (FIG. 11). Furthermore, there is no evidence for UBC silencing although previous knock-out studies as well as work herein have shown that cells can tolerate silencing of UBB or UBC separately.

Together, these findings provide a rationale for the development of a medicine targeting UBC at the mRNA level that might include siRNA therapeutics (Goldberg, et al., 2011; Zuckerman, et al., 2015), antisense oligonucleotides (Bennett, et al., 2016; McClorey, et al., 2015), or other approaches. In our studies, we see little to no toxicity caused by localized UBC silencing, though tolerance for systemic silencing of UBC remains untested. While acute knockdown of UBC in cells expressing normal levels of UBB can lead to a transient proliferative delay of hyperproliferative cell lines in vitro, $UBC^{+/-}$ heterozygous mice appear normal (Ryu, et al., 2007). These observations warrant further studies to exploit this important therapeutic opportunity for a large population of cancer patients lacking targets for precision medicine.

Our findings provide a new perspective on previous reports of synthetic lethality among functional paralogs involved in likely compensatory roles in fitness. These include ARID1A and ARID1B (Helming, et al., 2014), SMARCA2 and SMARCA4 (Hoffman, et al., 2014; Oike, et al., 2013) and most recently CBP and p300 (Kadoch, 2014; Ogiwara, et al., 2013). Although the roles of these genes in tumorigenesis remains to be elucidated, these potent examples of synthetic lethality can now be expanded to include UBB, a ubiquitin-encoding gene that serves as a biomarker for a clinically aggressive ovarian cancer subtype, and its paralog UBC. Our observation offers new insight for the development of targeted agents in a newly defined patient population.

INCORPORATION BY REFERENCE

All references cited herein, including patents, patent applications, papers, publications, text books, and the like, and the references cited therein, to the extent that they are not already, are hereby incorporated herein by reference in their entirety.

REFERENCES

1. Pagliarini R, Shao W, Sellers W R. Oncogene addiction: pathways of therapeutic response, resistance, and road maps toward a cure. EMBO reports. 2015; 16:280-96.
2. McLornan D P, List A, Mufti G J. Applying Synthetic Lethality for the Selective Targeting of Cancer. New England Journal of Medicine. 2014; 371:1725-35.
3. Bitler B G, Aird K M, Garipov A, Li H, Amatangelo M, Kossenkov A V, et al. Synthetic lethality by targeting EZH2 methyltransferase activity in ARID1A-mutated cancers. Nature medicine. 2015; 21:231-8.
4. van den Bent M J. Interobserver variation of the histopathological diagnosis in clinical trials on glioma: a clinician's perspective. Acta Neuropathol. 2010; 120:297-304.

5. Verhaak R G, Hoadley K A, Purdom E, Wang V, Qi Y, Wilkerson M D, et al. Integrated genomic analysis identifies clinically relevant subtypes of glioblastoma characterized by abnormalities in PDGFRA, IDH1, EGFR, and NF1. Cancer Cell. 2010; 17:98-110.
6. Parsons D W, Jones S, Zhang X, Lin J C, Leary R J, Angenendt P, et al. An integrated genomic analysis of human glioblastoma multiforme. Science. 2008; 321:1807-12.
7. Dang L, Yen K, Attar E C. IDH mutations in cancer and progress toward development of targeted therapeutics. Ann Oncol. 2016; 27:599-608.
8. Loehrer P J, Einhorn L H. Drugs five years later. Cisplatin. Ann Intern Med. 1984; 100:704-13.
9. Verhaak R G, Tamayo P, Yang J Y, Hubbard D, Zhang H, Creighton C J, et al. Prognostically relevant gene signatures of high-grade serous ovarian carcinoma. The Journal of clinical investigation. 2013; 123:517-25.
10. Zhang H, Liu T, Zhang Z, Payne S H, Zhang B, McDermott J E, et al. Integrated Proteogenomic Characterization of Human High-Grade Serous Ovarian Cancer. Cell. 2016; 166:755-65.
11. Winterhoff B, Hamidi H, Wang C, Kalli K R, Fridley B L, Dering J, et al. Molecular classification of high grade endometrioid and clear cell ovarian cancer using TCGA gene expression signatures. Gynecol Oncol. 2016; 141:95-100.
12. Kim G, Ison G, McKee A E, Zhang H, Tang S, Gwise T, et al. FDA Approval Summary: Olaparib Monotherapy in Patients with Deleterious Germline BRCA-Mutated Advanced Ovarian Cancer Treated with Three or More Lines of Chemotherapy. Clinical cancer research: an official journal of the American Association for Cancer Research. 2015; 21:4257-61.
13. Lord C J, Tutt A N, Ashworth A. Synthetic lethality and cancer therapy: lessons learned from the development of PARP inhibitors. Annual review of medicine. 2015; 66:455-70.
14. Wiborg O, Pedersen M S, Wind A, Berglund L E, Marcker K A, Vuust J. The human ubiquitin multigene family: some genes contain multiple directly repeated ubiquitin coding sequences. EMBO J. 1985; 4:755-9.
15. Barretina J, Caponigro G, Stransky N, Venkatesan K, Margolin A A, Kim S, et al. The Cancer Cell Line Encyclopedia enables predictive modelling of anticancer drug sensitivity. Nature. 2012; 483:603-307.
16. Ryu K Y, Maehr R, Gilchrist C A, Long M A, Bouley D M, Mueller B, et al. The mouse polyubiquitin gene UbC is essential for fetal liver development, cell-cycle progression and stress tolerance. EMBO J. 2007; 26:2693-706.
17. Liu X, Erikson R L. Activation of Cdc2/cyclin B and inhibition of centrosome amplification in cells depleted of Plk1 by siRNA. Proceedings of the National Academy of Sciences of the United States of America. 2002; 99:8672-6.
18. Nijhawan D, Zack T I, Ren Y, Strickland M R, Lamothe R, Schumacher S E, et al. Cancer vulnerabilities unveiled by genomic loss. Cell. 2012; 150: 842-54.
19. Solimini N L, Xu Q, Mermel C H, Liang A C, Schlabach M R, Luo J, et al. Recurrent hemizygous deletions in cancers may optimize proliferative potential. Science. 2012; 337:104-9.
20. Claessen J H, Kundrat L, Ploegh H L. Protein quality control in the E R: balancing the ubiquitin checkbook. Trends in cell biology. 2012; 22:22-32.
21. Al-Hakim A, Escribano-Diaz C, Landry M C, O'Donnell L, Panier S, Szilard R K, et al. The ubiquitous role of ubiquitin in the DNA damage response. DNA repair. 2010; 9:1229-40.
22. Moldovan G L, D'Andrea A D. How the fanconi anemia pathway guards the genome. Annu Rev Genet. 2009; 43:223-49.
23. Paulsen R D, Soni D V, Wollman R, Hahn A T, Yee M C, Guan A, et al. A genome-wide siRNA screen reveals diverse cellular processes and pathways that mediate genome stability. Mol Cell. 2009; 35:228-39.
24. Stewart G S. Solving the RIDDLE of 53BP1 recruitment to sites of damage. Cell Cycle. 2009; 8:1532-8.
25. Stewart G S, Panier S, Townsend K, Al-Hakim A K, Kolas N K, Miller E S, et al. The RIDDLE syndrome protein mediates a ubiquitin-dependent signaling cascade at sites of DNA damage. Cell. 2009; 136:420-34.
26. Park H, Yoon M S, Ryu K Y. Disruption of polyubiquitin gene Ubc leads to defective proliferation of hepatocytes and bipotent fetal liver epithelial progenitor cells. Biochem Biophys Res Commun. 2013; 435:434-40.
27. Ryu K Y, Park H, Rossi D J, Weissman I L, Kopito R R. Perturbation of the hematopoietic system during embryonic liver development due to disruption of polyubiquitin gene Ubc in mice. PLoS one. 2012; 7:e32956.
28. Sinnar S A, Small C L, Evanoff R M, Reinholdt L G, Griswold M D, Kopito R R, et al. Altered testicular gene expression patterns in mice lacking the polyubiquitin gene Ubb. Mol Reprod Dev. 2011; 78:415-25.
29. Goldberg M S, Xing D, Ren Y, Orsulic S, Bhatia S N, Sharp P A. Nanoparticle-mediated delivery of siRNA targeting Parp1 extends survival of mice bearing tumors derived from Brca1-deficient ovarian cancer cells. Proceedings of the National Academy of Sciences of the United States of America. 2011; 108:745-50.
30. Zuckerman J E, Davis M E. Clinical experiences with systemically administered siRNA-based therapeutics in cancer. Nat Rev Drug Discov. 2015; 14: 843-56.
31. Bennett C F, Baker B F, Pham N, Swayze E, Geary R S. Pharmacology of Antisense Drugs. Annu Rev Pharmacol Toxicol. 2016.
32. McClorey G, Wood M J. An overview of the clinical application of antisense oligonucleotides for RNA-targeting therapies. Curr Opin Pharmacol. 2015; 24: 52-8.
33. Helming K C, Wang X, Wilson B G, Vazquez F, Haswell J R, Manchester H E, et al. ARID1B is a specific vulnerability in ARID1A-mutant cancers. Nature medicine. 2014; 20:251-4.
34. Hoffman G R, Rahal R, Buxton F, Xiang K, McAllister G, Frias E, et al. Functional epigenetics approach identifies BRM/SMARCA2 as a critical synthetic lethal target in BRG1-deficient cancers. Proceedings of the National Academy of Sciences of the United States of America. 2014; 111:3128-33.
35. Oike T, Ogiwara H, Tominaga Y, Ito K, Ando O, Tsuta K, et al. A synthetic lethality-based strategy to treat cancers harboring a genetic deficiency in the chromatin remodeling factor BRG1. Cancer research. 2013; 73:5508-18.
36. Kadoch C. Lifting Up the HAT: Synthetic Lethal Screening Reveals a Novel Vulnerability at the CBP-p300 Axis. Cancer discovery. 2016; 6:350-2.
37. Ogiwara H, Sasaki M, Mitachi T, Oike T, Higuchi S, Tominaga Y, et al. Targeting p300 Addiction in CBP-Deficient Cancers Causes Synthetic Lethality by Apoptotic Cell Death due to Abrogation of MYC Expression. Cancer discovery. 2016; 6:430-45.

38. Schmittgen T D, Livak K J. Analyzing real-time PCR data by the comparative C(T) method. Nature protocols. 2008; 3:1101-8.
39. Cancer Genome Atlas Research N, Weinstein J N, Collisson E A, Mills G B, Shaw K R, Ozenberger B A, et al. The Cancer Genome Atlas Pan-Cancer analysis project. Nature genetics. 2013; 45:1113-20.
40. Li B, Dewey C N. RSEM: accurate transcript quantification from RNA-Seq data with or without a reference genome. BMC bioinformatics. 2011; 12:323.
41. Consortium G T. Human genomics. The Genotype-Tissue Expression (GTEx) pilot analysis: multitissue gene regulation in humans. Science. 2015; 348:648-60.
42. Fraley C, Raftery, A. E., Murphy, T. B., Scrucca, L. mclust Version 4 for R: Normal Mixture Modeling for Model-Based Clustering, Classification, and Density Estimation. University of Washington. 2012; Dept of Statistics: 1-57.
43. Therneau TaL, T. A Package for Survival Analysis in S. version 2.38. http://CRANR-projectorg/package=survival 2015.
44. Sheng Q, Liu X, Fleming E, Yuan K, Piao H, Chen J, et al. An activated ErbB3/NRG1 autocrine loop supports in vivo proliferation in ovarian cancer cells. Cancer Cell. 2010; 17:298-310.
45. Chojnacki M, et al. Characterizing polyubiquitinate d forms of the neurodegenerative ubiquitin mutant UBB+1. FEBS Letters. 2016; 590:4573-4585.

What is claimed is:

1. A method of treating a patient having cancer, comprising
identifying a patient having cancer with (i) a reduced expression level of a ubiquitin B (UBB) gene product or (ii) a ratio of an expression level of a ubiquitin C (UBC) gene product to an expression level of a ubiquitin B (UBB) gene product that is greater than 1.25, and
administering to the patient a therapeutically effective amount of a ubiquitin C (UBC) antagonist.

2. The method of claim 1, wherein the cancer is selected from the group consisting of uterine sarcoma, endometrial carcinoma, and ovarian adenocarcinoma.

3. The method of claim 1, wherein the cancer is ovarian adenocarcinoma.

4. The method of claim 1, comprising measuring the copy number of the UBB gene in a sample of the patient.

5. The method of claim 1, comprising measuring the expression level of the UBB gene product or the expression level of the UBC gene product in a sample of the patient.

6. The method of claim 1, comprising administering to the patient a chemotherapeutic drug.

7. The method of claim 6, wherein the chemotherapeutic drug is cisplatin.

8. The method of claim 6, wherein the chemotherapeutic drug causes a DNA damage response (DDR) in the patient.

9. The method of claim 1, wherein the UBC antagonist is an anti-sense nucleic acid, a short hairpin RNA (shRNA) or a short inhibitory RNA (siRNA).

10. The method of claim 9, wherein the shRNA targets the nucleic acid sequence set forth in SEQ ID NO: 1.

11. The method of claim 1, wherein the UBC antagonist is a compound.

12. The method of claim 11, wherein the UBC antagonist is a small molecule compound.

* * * * *

```
                        SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
cgagaacgtc aaagcaaaga t                                            21

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
atcacagaat cgtcgtatgc a                                            21

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cgatactacc tacggcaaat t                                            21

<210> SEQ ID NO 4
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
tggtttacat gtcgactaa                                               19

<210> SEQ ID NO 5
```

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
caaggctgtt agagagataa ttgga                                      25

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
gacccaagct ggctagttaa g                                          21

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
cctcaagggt gatggtcttg                                            20

<210> SEQ ID NO 8
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 8
aggcaccatg cagatcttcg tgaa                                       24

<210> SEQ ID NO 9
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gcctacagag aagcagtatg ag                                         22

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
```
agagggcata caaggcattt                                                    20

<210> SEQ ID NO 11
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
aagccttgtt ggcacaggaa tgc                                                23

<210> SEQ ID NO 12
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
guaagaccau cacucucga                                                     19

<210> SEQ ID NO 13
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gugaagaccc ugacuggua                                                     19

<210> SEQ ID NO 14
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aagcaaagau ccaggacaa                                                     19

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gugaagacuc ugacuggua                                                     19

<210> SEQ ID NO 16
<211> LENGTH: 21
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 16
gaggttgatc tttgccggaa a                                              21

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gaggttgatc tttgctggga a                                              21

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
taaaggtttc gttgcatggt a                                              21

<210> SEQ ID NO 19
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ucgaaaaugu gaaggccaa                                                 19

<210> SEQ ID NO 20
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
tcaagtgacg atcacagcg                                                 19

<210> SEQ ID NO 21
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cgctgtgatc gtcacttga                                                 19
```

```
<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ttattgaaag gaaagtgca                                                19

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
tgcactttcc tttcaataa                                                19

<210> SEQ ID NO 24
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Arg Gly Asp Ser
1
```